(12) United States Patent
Balachandran et al.

(10) Patent No.: US 9,808,171 B2
(45) Date of Patent: Nov. 7, 2017

(54) UTILIZATION OF ELECTRODE SPATIAL ARRANGEMENTS FOR CHARACTERIZING CARDIAC CONDUCTION CONDITIONS

(71) Applicant: St. Jude Medical, Atrial Fibrillation Division, Inc., St. Paul, MN (US)

(72) Inventors: Ram K. Balachandran, Maple Grove, MN (US); D. Curtis Deno, Andover, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 14/782,134

(22) PCT Filed: May 7, 2014

(86) PCT No.: PCT/US2014/037160
§ 371 (c)(1),
(2) Date: Oct. 2, 2015

(87) PCT Pub. No.: WO2014/182822
PCT Pub. Date: Nov. 13, 2014

(65) Prior Publication Data
US 2016/0045133 A1 Feb. 18, 2016

Related U.S. Application Data

(60) Provisional application No. 61/855,058, filed on May 7, 2013.

(51) Int. Cl.
*A61B 5/04* (2006.01)
*A61B 5/042* (2006.01)
(Continued)

(52) U.S. Cl.
CPC .......... *A61B 5/0422* (2013.01); *A61B 5/0452* (2013.01); *A61B 5/061* (2013.01);
(Continued)

(58) Field of Classification Search
None
See application file for complete search history.

(56) References Cited

U.S. PATENT DOCUMENTS

| 5,297,549 A | 3/1994 | Beatty et al. |
| 5,848,972 A | 12/1998 | Triedman et al. |

(Continued)

FOREIGN PATENT DOCUMENTS

| EP | 1166714 | 1/2002 |
| EP | 1336379 | 8/2003 |

(Continued)

OTHER PUBLICATIONS

Mironov, Sergey et al.; "Role of Conduction Velocity Restitution and Short-Term Memory in the Development of Action Potential Duration Alternans in Isolated Rabbit Hearts"; Circulation; pp. 17-25; Jul. 1, 2008.

(Continued)

*Primary Examiner* — Ankit D Tejani
(74) *Attorney, Agent, or Firm* — Dykema Gossett PLLC

(57) ABSTRACT

A system and method are provided for determining electrophysiological data. The system comprises an electronic control unit that is configured to receive electrical signals from a set of electrodes, receive position and orientation data for the set of electrodes from a mapping system, compensate for position and orientation artifacts of the set of electrodes, compose cliques of a subset of neighboring electrodes in the set of electrodes, determine catheter orientation independent information of a target tissue, and output the orientation independent information to a display. The method comprising receiving electrogram data for a set of electrodes (80), compensating for artifacts in sensor positions in the mapping system (81), resolving the bipolar signals into a 3D vector electrogram in the mapping system coordinates (82), manipulating observed unipolar voltage signals and the (Continued)

tangent component of the e-field to estimate the conduction velocity vector (83), and outputting the catheter orientation independent information (84).

20 Claims, 14 Drawing Sheets

(51) Int. Cl.
| | | |
|---|---|---|
| *A61B 5/0452* | (2006.01) | |
| *A61B 5/06* | (2006.01) | |
| *A61B 18/14* | (2006.01) | |
| *A61B 5/00* | (2006.01) | |
| *A61B 17/00* | (2006.01) | |
| *A61B 18/00* | (2006.01) | |
| *A61B 34/20* | (2016.01) | |

(52) U.S. Cl.
CPC ........ *A61B 5/7203* (2013.01); *A61B 18/1492* (2013.01); *A61B 34/20* (2016.02); *A61B 5/062* (2013.01); *A61B 5/7239* (2013.01); *A61B 2017/00039* (2013.01); *A61B 2017/00044* (2013.01); *A61B 2017/00053* (2013.01); *A61B 2018/00577* (2013.01); *A61B 2018/00839* (2013.01); *A61B 2034/2051* (2016.02); *A61B 2034/2053* (2016.02); *A61B 2218/002* (2013.01)

(56) References Cited

U.S. PATENT DOCUMENTS

| | | | |
|---|---|---|---|
| 5,921,923 | A | 7/1999 | Kuck et al. |
| 6,233,476 | B1 | 5/2001 | Strommer et al. |
| 6,360,121 | B1 | 3/2002 | Shoda et al. |
| 6,400,981 | B1* | 6/2002 | Govari ............... A61B 5/0422 600/509 |
| 6,498,944 | B1 | 12/2002 | Ben-Haim et al. |
| 6,546,270 | B1 | 4/2003 | Goldin et al. |
| 6,690,963 | B2 | 2/2004 | Ben-Haim et al. |
| 6,788,967 | B2 | 9/2004 | Ben-Haim et al. |
| 7,197,354 | B2 | 3/2007 | Sobe |
| 7,263,397 | B2 | 8/2007 | Hauck et al. |
| 7,386,339 | B2 | 6/2008 | Strommer et al. |
| 8,862,213 | B2 | 10/2014 | Lo et al. |
| 8,876,817 | B2 | 11/2014 | Avitall et al. |
| 2006/0253030 | A1 | 11/2006 | Altmann et al. |
| 2007/0225589 | A1* | 9/2007 | Viswanathan ......... A61B 5/042 600/407 |
| 2008/0221643 | A1 | 9/2008 | Olson |
| 2009/0248014 | A1* | 10/2009 | Shachar ............... A61B 5/0402 606/41 |
| 2010/0168557 | A1 | 7/2010 | Deno et al. |
| 2010/0168560 | A1 | 7/2010 | Hauck et al. |
| 2013/0190747 | A1 | 7/2013 | Koblish et al. |
| 2013/0274582 | A1 | 10/2013 | Afonso et al. |
| 2014/0058375 | A1 | 2/2014 | Koblish |
| 2014/0336518 | A1 | 11/2014 | Shuros et al. |

FOREIGN PATENT DOCUMENTS

| | | |
|---|---|---|
| EP | 2186474 | 5/2010 |
| JP | 11047148 A | 2/1999 |
| JP | 2001-061789 | 3/2001 |
| JP | 2002-051998 | 2/2002 |
| JP | 2007537831 A | 12/2007 |
| JP | 2012524606 A | 10/2012 |
| WO | 97/24983 | 7/1997 |
| WO | 2012/037471 | 3/2012 |
| WO | 2012/092016 | 7/2012 |
| WO | 2014/113612 | 7/2014 |
| WO | 2014/182822 | 11/2014 |

OTHER PUBLICATIONS

Mountantonakis, Stavros E. et al.; "Relationship between Voltage Map "Channels" and the Location of Critical Isthmus Sites in Patients with Post-Infarction Cardiomyopathy and Ventricular Tachycardia"; JACC; vol. 61; No. 20; pp. 2088-2095; May 21, 2013.

Nanthakumar, Kumaraswamy et al.; "Regional Differences in Ventricular Fibrillation in the Open-Chest Porcine Left Ventricle"; Circulation Research; pp. 734-740; Oct. 18, 2002.

Narayen, Sanjiv M. et al.; "Treatment of Atrial Fibrillation by the Ablation of Localized Sources"; JACC; vol. 60; No. 7; pp. 628-636; Aug. 14, 2012.

Nayyar, Sachin et al.; "High-Density Mapping of Ventricular Scar a Comparison of Ventricular Tachycardia (VT) Supporting Channels with Channels that do not Support VT"; Circulation; pp. 90-98; Feb. 2014.

Otomo, Kiyoshi et al.; "Local Unipolar and Bipolar Electrogram Criteria for Evaluating the Transmurality of Atrial Ablation Lesions at Different Catheter Orientations Relative to the Endocardial Surface"; Heart Rhythm; vol. 7; No. 9; pp. 1291-1300; Sep. 2010.

Parson, Ian D. et al.; "Cardiac Mapping Instrumentation for the Instantaneous Display of Endocardial and Epicardial Activation"; IEEE Transactions on Biomedical Engineering; vol. BME-34; No. 6; pp. 468-472; Jun. 1987.

Patel, Parin J. et al.; "Electroanatomic Mapping of the Intercaval Bundle in Atrial Fibrillation"; Circulation; pp. 1262-1267; Dec. 2014.

Pieper, Carl F. et al.; "Simultaneously Collected Monopolar and Discrete Bipolar Electrograms: Comparison of Activation Time Detection Algorithms"; PACE; vol. 16; pp. 426-433; Mar. 1993.

Plank, G. et al.; "Modal Study of Vector-Loop Morphology During Electrical Mapping of Microscopic Conduction in Cardiac Tissue"; Annals of Biomedical Engineering; vol. 28; No. 10; pp. 1244-1252; Oct. 2000.

Plank, G. et al.; "Use of Cardiac Electric Near-Field Measurements to Determine Activation Times"; Annals of Biomedical Engineering; vol. 31; No. 9; pp. 1066-1076; Oct. 2003.

Plank, G. et al.; "Cardiac Near-Field Morphology During Conduction Around a Microscopic Obstacle-a Computer Simulation Study"; Annals of Biomedical Engineering; vol. 31; No. 10; pp. 1206-1212; Nov. 2003.

Price, Adam et al.; "Novel Ablation Catheter Technology that Improves Mapping Resolution and Monitoring of Lesion Maturation"; The Journal of Innovations in Cardiac Rhythm Management; pp. 599-609; Jan. 2012.

Ravelli, Flavia et al.; "Wave Similarity Mapping Shows the Spatiotemporal Distribution of Fibrillatory Wave Complexity in the Human Right Atrium During Paroxysmal and Chronic Atrial Fibrillation"; Journal of Cardiovascular Electrophysiology; vol. 16; No. 10; pp. 1071-1076; Oct. 2005.

Schilling, Richard J. et al.; "Simultaneous Endocardial Mapping in the Human Left Ventricle Using a Noncontact Catheter"; Circulation; pp. 887-898; Sep. 1, 1998.

Schuler, S. et al.; "Influence of Catheter Orientation, Tissue Thickness and Conduction Velocity on the Intracardiac Electrogram"; Biomedizinische Technik/Biomedical Engineering; Sep. 2013.

Schumacher, Burghard et al.; "Transverse Conduction Capabilities of the Crista Terminalis in Patients with Atrial Flutter and Atrial Fibrillation"; JACC. vol. 34; No. 2; pp. 363-373; Aug. 1999.

Shors, Stephanie M. et al. "A method for Determining High-Resolution Activation Time Delays in Unipolar Cardiac Mapping"; IEEE Transactions on Biomedical Engineering; vol. 43; No. 12; pp. 1192-1196; Dec. 1996.

Spears, Danna A. et al.; "Relationship of Bipolar and Unipolar Electrogram Voltage to Scar Transmurality and Composition Derived by Magnetic Resonance Imaging in Patients with Nonischemic Cardiomyopathy Undergoing VT Ablation"; Heart Rhythm; vol. 9; No. 11; pp. 1837-1846; Nov. 2012.

Stevenson, William G. et al.; "Recording Techniques for Clinical Electrophysiology"; Journal of Cardiovascular Electrophysiology; vol. 16; No. 9; pp. 1017-1022; Sep. 2005.

(56) References Cited

OTHER PUBLICATIONS

Tedrow, Usha B. et al.; "Recording and Interpreting Unipolar Electrograms to Guide Catheter Ablation"; Heart Rhythm; vol. 8; No. 5; pp. 791-796; May 2011.
Thompson, Nathaniel C. et al.; "Improved Spatial Resolution and Electrogram Wave Direction Independence with the Use of an Orthogonal Electrode Configuration" J Clin Monit Comput; pp. 157-163; Apr. 2014.
Tungjitkusolmun, Supan et al.; "Guidelines for Predicting Lesion Size at Common Endocardial Locations During Radio-Frequency Ablation"; IEEE Transactions on Biomedical Engineering; vol. 48; No. 2; pp. 194-201; Feb. 2001.
Weber, Frank M. et al.; "Conduction Velocity Restitution of the Human Atrium-An Efficient Measurement Protocol for Clinical Electrophysiological Studies"; IEEE Transactions on Biomedical Engineering; vol. 58; No. 9; pp. 2648-2655; Sep. 2011.
Weber, Frank M. et al.; "Wave-Direction and Conduction-Velocity Analysis from Intracardiac Electrograms-a Single-Shot Technique"; IEEE Transactions on Biomedical Engineering; vol. 57; No. 10; pp. 2394-2401; Oct. 2010.
Witkowski, Francis X. et al.; "In Vivo Estimation of Cardiac Transmembrane Current"; Circulation Research; vol. 72; No. 2; pp. 424-439; Feb. 1993.
Zaman, Junaid, A.B. et al.; "The Rotor Revolution Conduction at the Eye of the Storm in Atrial Fibrillation"; Circulation; pp. 1230-1236; Dec. 2014.
Zhang, Xin et al.; "Noninvasive Three-Dimensional Electrocardiographic Imaging of Ventricular Activation Sequence"; AJP-Heart Circ Physiol; vol. 289; pp. H2724-H2732; Aug. 5, 2006.
Kearsley, Simon K.; "On the Orthogonal Transformation Used for Structural Comparisons"; Acta Crystallographica Section A; A45; pp. 208-210; Feb. 1, 1989.
Kumar, Saurabh et al.; "Unipolar Electrogram Morphology to Assess Lesion Formation During Catheter Ablation of Atrial Fibrillation Successful Translation into Clinical Practice"; Circ Arrhythm Electrophysiol; pp. 1050-1052; Dec. 2013.
Burch, George E. et al.; "Chapter X The Development of Spatial Vectrocardiography"; A History of Electrocardiography; Norman Publishing; pp. 235-248; Apr. 1990.
Gupta, Sanjaya et al.; "Rapid Ablation of Recurrent Atrial Flutter Using a Novel Ablation Catheter"; The Journal of Innovations in Cardiac Rhythm Management; No. 5; pp. 1808-1812; Nov. 2014.
Yamada, Takumi; "Pulmonary Vein Isolation with a Multielectrode Basket Cather"; Indian Pacing and Electrophysiology Journal; pp. 97-109; Apr. 2007.
Yamada, Takumi et al.; "Electrophysiological Pulmonary Vein Antrum Isolation with a Multielectrode Basket Catheter is Feasible and Effective for Curing Paroxysmal Atrial Fibrillation: Efficacy of Minimally Extensive Pulmonary Vein Isolation"; Heart Rhythm, vol. 3; No. 4; pp. 377-384; Apr. 2006.
Schmitt, Otto H. et al.; "Symposium on Electrocardiography and Vectorcardiography the Present Status of Vectorcardiography"; JAMA Internal Medicine; vol. 96; No. 5; pp. 574-590; Nov. 1955.
Lindsay, Bruce D. et al.; "Novel Directional Activation Map Using Local Propagation Between Adjacent Electrograms"; Heart Rhythm; vol. 8; No. 5; May Supplement 2011.
Fedotov, N.M. et al.; "Methods for Increasing the Reliability of Coordinate Determination by the Location and Imaging Systems of Endocardial Electrodes"; Biomedical Engineering; vol. 41, No. 4; pp. 145-149; Jul. 1, 2007.
Gaudette; RJ et al.; "Epicardial Velocity Estimation Using Wavelets"; Computers in Cardiology; vol. 24; pp. 339-342; Sep. 7, 1997.
Rogers, Jack M. et al.; "Quantitative Techniques for Analyzing High-Resolution Cardiac-Mapping Data"; IEEE Engineering in Medicine and Biology; vol. 17, No. 1; pp. 62-72; Jan. 1, 1998.
Anter, Elad et al.; High-Resolution Mapping of Scar-Related Atrial Arrhythmias Using Smaller Electrodes with Closer Interelectrode Spacing; Circulation; vol. 8; No. 3, Jun. 2015.
Arora, Rishi et al.; "Fundamentals of Intracardiac Mapping"; Catheter Ablation of Cardiac Arrhythmias; pp. 107-134; 2006.

Avitall, Boaz et al.; "Maximal Electrogram Attenuation Recorded from Mini Electrodes Embedded on 4.5-mm Irrigated and 8-mm Nonirrigated Catheters Signifies Lesion Maturation"; Journal of Cardiovascular Electrophysiology; vol. 26; No. 2; Feb. 2015.
Balasundaram, Krishnanand et al.; "Tracking Rotors with Minimal Electrodes: Modulation Index Based Strategy"; Circulation; vol. 8; No. 2; Apr. 2015.
Barnette, AR et al.; "Estimation of a 3-D Conduction Velocity Vector Fields from Cardiac Mapping Data"; Computers in Cardiology; vol. 25; pp. 605-608; Sep. 1998.
Bayly, Philip V. et al.; "Estimation of Conduction Velocity Vector Fields from Epicardial Mapping Data"; IEEE Transactions on Biomedical Engineering; vol. 45; No. 5; pp. 563-569; May 1998.
Bayly, PV et al.; "Estimation of Conduction Velocity Vector Fields from 504-Channel Epicardial Mapping Data"; Computers in Cardiology; pp. 133-136; Sep. 1996.
Benharash, Peyman et al.; "Quantitative Analysis of Localized Sources Identified by Focal Impulse and Rotor Modulation Mapping in Atrial Fibrillation"; Circulation; pp. 554-561; Jun. 2015.
Bharati, Saroja et al.; "The Conduction System of the Swine Heart"; Chester; vol. 100; No. 1; pp. 207-212; Jul. 1991.
Bartone, Agustin et al.; "Unipolar Signal Modification as a Guide for Lesion Creation During Radiofrequency Application in the Left Atrium Prospective Study in Humans in the Setting of Paroxysmal Atrial Fibrillation Catheter Ablation"; Circulation; pp. 1096-1102; Dec. 2013.
Bouman, L.N. et al.; "Structure and Function of the Sino-Atrial Node: A Review"; European Heart Journal; vol. 7; No. 2; pp. 94-104; Feb. 1986.
Boyett, M.R. et al.; "The Sinoatrial Node, a Heterogeneous Pacemaker Structure"; Cardiovascular Research; vol. 47; No. 4; Sep. 2000.
Cantwell, C.D. et al.; "Techniques for Automated Local Activation Time Annotation and Conduction Velocity Estimation in Cardiac Mapping"; Computers in Biology and Medicine; Oct. 1, 2015.
de Bakker, Jacquest M.T. et al.; "Activation Mapping: Unipolar Versus Bipolar Recording"; Cardiac Electrophysiology from Cell to Bedside Second Edition; pp. 1068-1078; Jan. 28, 1995.
Casella, Michela et al.; "Feasibility of Combined Unipolar and Bipolar Voltage Maps to Improve Sensitivity of Endomycardial Biopsy"; Circulation; Jun. 2015.
Chan, Rodrigo C. et al.; "The Effect of Ablation Length and Catheter Tip to Endocardial Orientation on Radiofrequency Lesion Size in the Canine Right Atrium"; PACE; vol. 25; No, 1; Jan. 2002.
de Bakker, Jacques M.T. et al.; "The Pathophysiologic Basis of Fractionated and Complex Electrograms and the Impact of Recording Techniques on Their Detection and Interpretation"; Circulation; vol. 3; No. 2; Apr. 2010.
Kadish, Alan H. et al.; "Vector Mapping of Myocardial Activation"; Circulation; vol. 74; No. 3; pp. 603-615 Sep. 1986.
Damle, Roger S.; "Atrial and Accessory Pathway Activation Direction in Patients with Orthodromic Supraventricular Tachycardia: Insights from Vector Mapping" JACC; vol. 23; No. 3; pp. 634-692; Mar. 1, 1994.
Deng, Dong-dong et al.; "Simulation of Biatrial Conduction via Different Pathways during Sinus Rhythm with a Detailed Human Atrial Model", Journal of Zhjiang University-Science B (Biomedicine & Biotechnology; pp. 676-694; Sep. 2012.
Deng, Dongdong et al.; "An Image-Based Model of the Whole Human Heart with Detailed Anatomical Structure and Fiber Orientation"; Compuutational and Mathematical Methods in Medicine; vol. 2012; Jul. 2012.
Desai, Jawahar M. et al.; "Two Phase Radiofrequency Catheter Ablation of Isolated Ventricular Endomyocardium"; PACE, vol. 14; pp. 1179-1194; Jul. 1991.
Dubois, R. et al.; "Global and Directional Activation Maps for Cardiac Mapping in Electrophysiology"; Computing in Cardiology; pp. 349-352; Sep. 2012.
Faes, Luca et al.; "A Method for Quantifying Atrial Fibrillation Organization Based on Wave-Morphology Similarity"; IEEE Transactions on Biomedical Engineering; vol. 49; No. 12; pp. 1504-1513; Dec. 2002.

(56) References Cited

OTHER PUBLICATIONS

Fisher, Westby G. et al.; "Three-Dimensional Electrogram Mapping Improves Ablation of Left-Sided Accessory Pathways"; PACE; vol. 15; pp. 2344-2356; Dec. 1992.

Fitzgerald, Tamara N. et al.; "Identification of Cardiac Rhythm Features by Mathematical Analysis of Vector Fields"; IEEE Transactions on Biomedical Engineering; vol. 52; No. 1; pp. 19-29; Jan. 2005.

Fitzgerald, Tamara N. et al.; "Comparative Psychometric Analysis of Vector and Isochrone Cardiac Activation Maps"; IEEE Transactions on Biomedical Engineering; vol. 51; No. 5; pp. 847-855; May 2004.

Fitzgerald; Tamara N. et al.; "Estimation of Cardiac Conduction Velocities Using Small Data Sets"; Annals of Biomedical Engineering; vol. 31; pp. 250-261; Mar. 2003.

Gerstenfeld, Edward P. et al.; "Evidence for Transient Linking of Atrial Excitation During Atrial Fibrillation in Humans"; Circulation; vol. 86; No. 2; pp. 375-382; Aug. 1992.

Gerstenfeld, Edward P. et al.; "Detection of Changes in Atrial Endocardial Activation with Use of an Orthogonal Catheter"; JACC; vol. 18; No. 4; pp. 1034-1042; Oct. 1991.

Gornick, Charles C. et al.; "Validation of a New Noncontact Catheter System for Electroanatomic Mapping of Left Ventricular Endocardium"; Circulation; pp. 829-835; Feb. 16, 1999

Haddad, El et al.; "Novel Algorithmic Methods in Mapping of Atrial and Ventricular Tachycardia"; Circulation; Jun. 2014.

Harrild, David M. et al.; "A Computer Model of Normal Conduction in the Human Atria"; Circulation Research; Sep. 29, 2000.

Horner, S.M. et al.; "Electrode for Recording Direction of Activation, Conduction Velocity, and Monophasic Action Potential of Myocardium"; the American Physiological Society; pp. H1917-H1927; Apr. 1997.

Huang, Jian et al.; "Evolution of the Organization of Epicardial Activation Patterns During Ventricular Fibrillation"; Journal of Cardiovascular Electrophysiology; vol. 9, No. 12; Dec. 1998.

Ideker, Raymond E. et al.; "The Assumptions of Isochronal Cardiac Mapping"; PACE; vol. 12; pp. 456-478; Mar. 1989.

Irie, Tadanobu et al.; "Relationship Between Sinus Rhythm Late Activation Zones and Critical Sites for Scar-Related Ventricular Tachycardia: a Systematic Analysis of Isochronal Late Activation Mapping"; Circulation; Apr. 2015.

Kadish, Alan et al..; "Mapping of Atrial Activation with a Noncontact, Multielectrode Catheter in Dogs"; Circulation; pp. 1906-1913; Apr. 13, 1999.

Kadish, Alan H. et al.; "Vector Mapping of Myocardial Activation"; Circulation; vol. 74; No. 3; pp. 603-615; Sep. 1986.

Karney, Charles F.F. et al.; "Quaternions in Molecular Modeling"; Journal of Molecular Graphics and Modeling; pp. 595-604; Jan. 2007.

Kay, Matthew W. et al.; "Measuring Curvature and Velocity Vector Fields for Waves of Cardiac Excitation in 2-D Media"; IEEE Transactions on Biomedical Engineering; vol. 52; No. 1; pp. 50-63; Jan. 2005.

Kumar, Saurabh et al.; Unipolar Electrogram Morphology to Assess Lesion Formation During Catheter Ablation of Atrial Fibrillation Successful Translation into Clinical Practice; Circulation; pp. 1050-1052; Dec. 2013.

Liu, Chenguang et al.; "Three-Dimensional Imaging of Ventricular Activation and Electrograms from Intracavity Recordings"; IEEE Transactions on Biomedical Engineering; vol. 58; No. 4; pp. 868-875; Apr. 2011.

Liu, Tu-Ying et al.; "Functional Characterization of the Crista Terminalis in Patients with Atrial Flutter: Implications of Radiofrequency Ablation"; JACC; vol. 43; No. 9; pp. 1639-1645; May 5, 2004.

Masse, M. et al.; "Velocity Field Analysis of Activation Maps in Atrial Fibrillation a Simulation Study"; World Congress on Medical Physics and Biomedical Engineering; vol. 25/4; pp. 1014-1017; Sep. 2009.

Mazeh, Nachaat et al.; "A Simplified Approach for Simultaneous Measurements of Wavefront Velocity and Curvature in the Heart Using Activation Times"; Cardiovascular Engineering and Technology; vol. 4; No. 4; Dec. 2013.

Michaud, Gregory F. et al.; "Information at our Catheter Tips: Unipolar Electrogram Morphology Makes another Comeback!"; Heart Rhythm; vol. 7; No. 9; pp. 1301-1302; Sep. 2010.

* cited by examiner

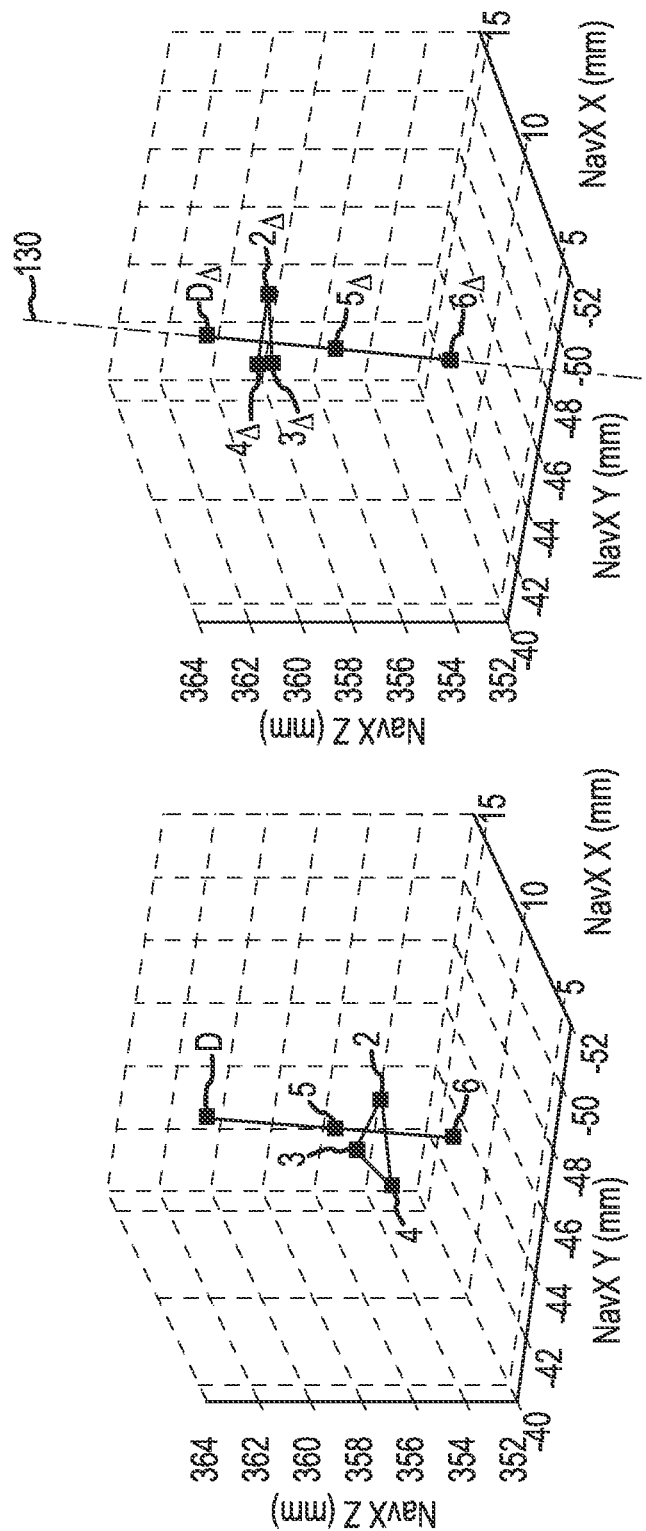

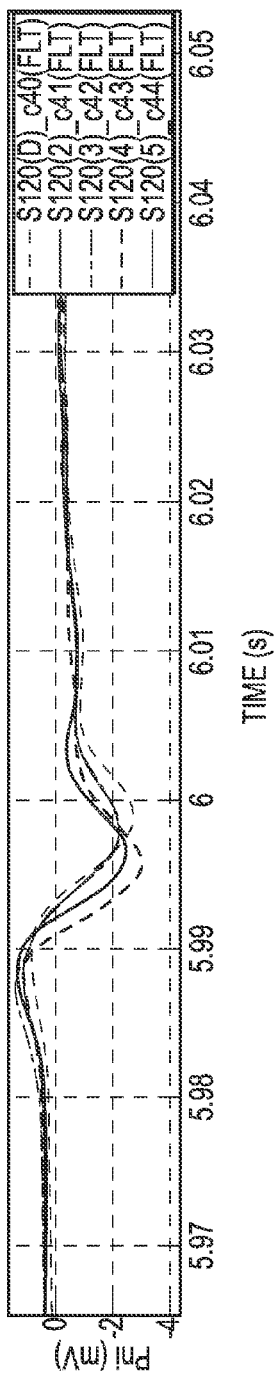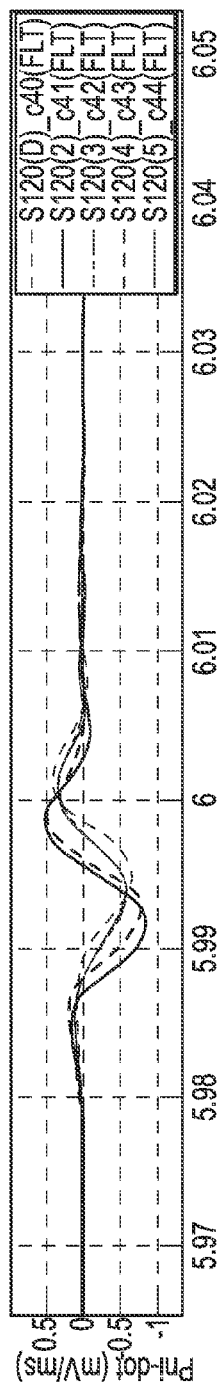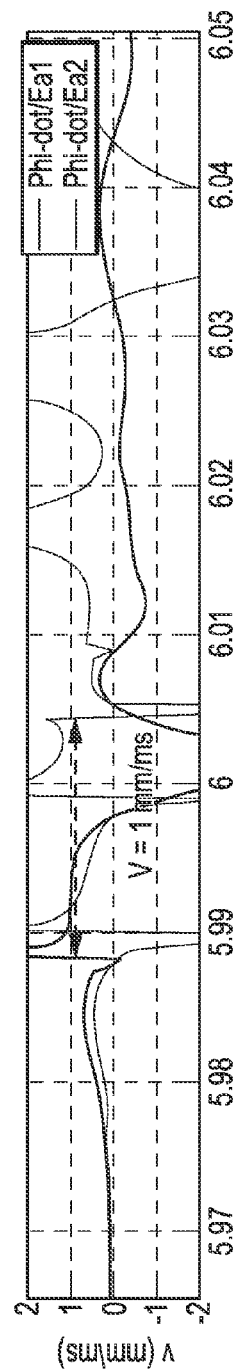

UTILIZATION OF ELECTRODE SPATIAL ARRANGEMENTS FOR CHARACTERIZING CARDIAC CONDUCTION CONDITIONS

CROSS-REFERENCE TO RELATED APPLICATIONS

This application claims the benefit of and priority to provisional U.S. patent application No. 61/855,058 filed 7 May 2013, which is hereby incorporated by reference as through fully set forth herein.

BACKGROUND a. Field

This disclosure relates to systems, apparatuses and methods for utilizing electrode spatial arrangements within a mapping system. In particular, the instant disclosure relates to systems, apparatuses and methods for characterizing cardiac conduction conditions in a catheter orientation independent manner using electrode spatial arrangements in 3D mapping systems.

b. Background

Electrophysiology (EP) catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. This lesion disrupts undesirable cardiac activation pathways and thereby limits, corrals, or prevents errant conduction signals that can form the basis for arrhythmias.

To position a catheter at a desired site within the body, some type of navigation may be used, such as using mechanical steering features incorporated into the catheter (or a sheath). In some examples, medical personnel may manually manipulate and/or operate the catheter using the mechanical steering features.

A navigating system may be used for visualization and to facilitate the advancement of catheters through a patient's vasculature to specific locations within the body. Such navigating systems may include, for example, electric and/or magnetic field based positioning and navigating systems that are able to determine the position and orientation of the catheter (and similar devices) within the body.

Conduction disorders in the body can result from abnormal conduction in regions as small as 1-4 mm. In addition, ablation in these regions must be restricted to the pathological tissue to preserve electrical and mechanical function, particularly with ventricular arrhythmias. Today, many catheters employ electrode pairs spaced greater than 4 mm apart which can make it difficult to reliably allow discrimination or localization of defects. Even when the electrodes are more closely spaced, around 1 mm to around 2 mm, the orientation of the pair of electrodes is a prominent factor in the amplitude and morphology of the resulting signals.

The foregoing discussion is intended only to illustrate the present field and should not be taken as a disavowal of claim scope.

BRIEF SUMMARY

In an embodiment, a system for determining electrophysiological data comprises an electronic control unit configured to receive electrogram data for a set of electrodes, receive position and orientation information for the set of electrodes from a mapping system, determine catheter orientation independent information of a tissue, and output the orientation independent information to the mapping system.

In another embodiment, a system for determining electrophysiological data comprises an electronic control unit that is configured to receive electrical signals from a set of electrodes, receive position and orientation data for the set of electrodes from a mapping system, compensate for position and orientation artifacts of the set of electrodes, compose cliques of a subset of neighboring electrodes in the set of electrodes, determine catheter orientation independent information of a target tissue, and output the orientation independent information to a display.

In another embodiment, a method of determining electrophysiological data includes receiving electrogram data for a set of electrodes, receiving position and orientation information for the set of electrodes from a mapping system, determining catheter orientation independent information of a tissue, and outputting orientation independent information.

BRIEF DESCRIPTION OF THE DRAWINGS

FIG. 7 is a plot of the electrode coordinates with artifacts for the segmented ring ablation catheter from FIGS. 2A and 2B that can be introduced when using an impedance based mapping system.

FIG. 8 is a plot of the corrected location of the electrode coordinates for the segmented ring ablation catheter from FIGS. 2A and 2B.

FIGS. 9-13 are plots of EP signals derived from the five distal most electrodes on the catheter of FIGS. 2A and 2B taken during a procedure.

DETAILED DESCRIPTION

The present disclosure relates to a system and method for utilizing electrode spatial arrangements within a mapping system. In particular, the instant disclosure relates to systems, apparatuses and methods for characterizing cardiac conduction conditions in a catheter orientation independent manner using electrode spatial arrangements in 3D mapping systems.

Figure 1:
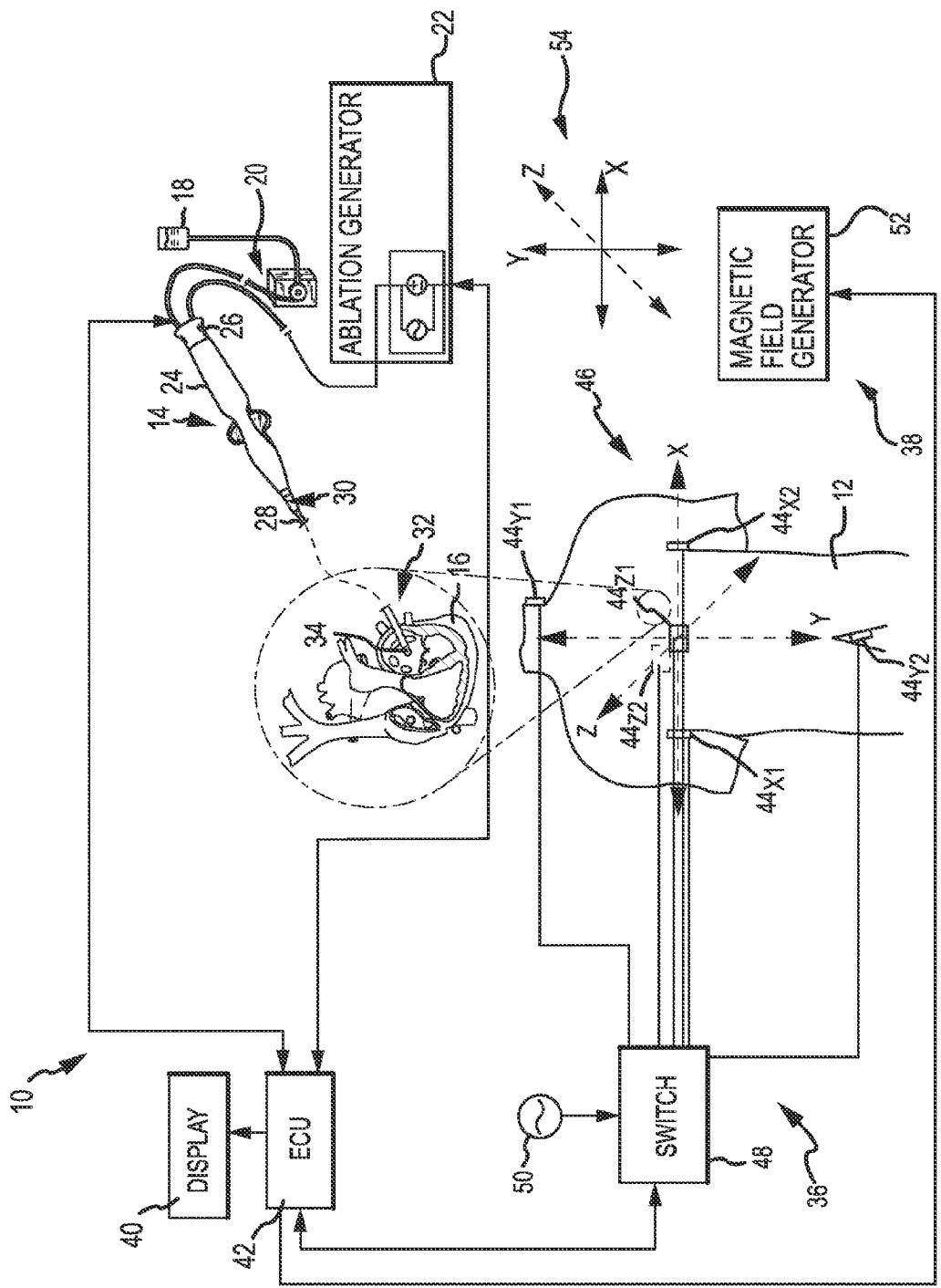
FIG. 1 is diagrammatic view of one embodiment of a system for navigating a medical device within a body.

Referring now to the figures, in which like reference numerals refer to the same or similar features in the various views, FIG. 1 illustrates one embodiment of a system 10 for navigating a medical device within a body 12. In the illustrated embodiment, the medical device comprises a catheter 14 that is shown schematically entering a heart, which is depicted in an exploded view away from the body 12 for purposes of illustration. The catheter 14, in this embodiment, is depicted as an irrigated radiofrequency (RF) ablation catheter for use in the treatment of cardiac tissue 16 in the body 12. It should be understood, however, that the system 10 may find application in connection with a wide variety of medical devices used within the body 12 for diagnosis or treatment. For example, the system 10 may be used to navigate an electrophysiological mapping catheter, an intracardiac echocardiography (ICE) catheter, or an ablation catheter using a different type of ablation energy (e.g., cryoablation, ultrasound, etc.). Further, it should be understood that the system 10 may be used to navigate medical devices used in the diagnosis or treatment of portions of the body 12 other than cardiac tissue 16.

Referring still to FIG. 1, the ablation catheter 14 is connected to a fluid source 18 for delivering a biocompatible irrigation fluid such as saline through a pump 20, which may comprise, for example, a fixed rate roller pump or variable volume syringe pump with a gravity feed supply from fluid source 18 as shown. The catheter 14 is also electrically connected to an ablation generator 22 for delivery of RF energy. The catheter 14 may include a handle 24; a cable connector or interface 26 at a proximal end of the handle 24; and a shaft 28 having a proximal end 30, a distal end 32, and one or more electrodes 34. The connector 26 provides mechanical, fluid, and electrical connections for conduits or cables extending from the pump 20 and the ablation generator 22. The catheter 14 may also include other conventional components not illustrated herein such as a temperature sensor, additional electrodes, and corresponding conductors or leads.

The handle 24 provides a location for the physician to hold the catheter 14 and may further provide means for steering or guiding the shaft 28 within the body 12. For example, the handle 24 may include means to change the length of one or more pull wires extending through the catheter 14 from the handle 24 to the distal end 32 of shaft 28. The construction of the handle 24 may vary.

The shaft 28 may be made from conventional materials such as polyurethane and may define one or more lumens configured to house and/or transport electrical conductors, pull wires, fluids, or surgical tools. The shaft 28 may be introduced into a blood vessel or other structure within the body 12 through a conventional introducer. The shaft 28 may then be steered or guided through the body 12 to a desired location such as the tissue 16 using guide wires or pull wires or other means known in the art including remote control guidance systems. The shaft 28 may also permit transport, delivery, and/or removal of fluids (including irrigation fluids and bodily fluids), medicines, and/or surgical tools or instruments.

The system 10 may include an electric-field-based positioning system 36, a magnetic-field-based positioning system 38, a display 40, and an electronic control unit (ECU) 42. Each of the exemplary system components is described further below.

The electric-field-based positioning system 36 is provided to determine the position and orientation of the catheter 14 and similar devices within the body 12. The system 36 may comprise, for example, the ENSITE NAVX system sold by St. Jude Medical, Inc. of St. Paul, Minn., and described in, for example, U.S. Pat. No. 7,263,397 titled "Method and Apparatus for Catheter Navigation and Location Mapping in the Heart," the entire disclosure of which is hereby incorporated by reference as though fully set forth herein. The system 36 operates based upon the principle that when low amplitude electrical current signals are passed through the thorax, the body 12 acts as a voltage divider (or potentiometer or rheostat) such that the electrical potential measured at one or more electrodes 34 on the catheter 14 may be used to determine the position of the electrodes, and, therefore, of the catheter 14, relative to a pair of external patch electrodes using Ohm's law and the relative location of a reference electrode (e.g., in the coronary sinus).

In the configuration shown in FIG. 1, the electric-field-based positioning system 36 further includes three pairs of patch electrodes 44, which are provided to generate electrical signals used in determining the position of the catheter 14 within a three-dimensional coordinate system 46. The electrodes 44 may also be used to generate EP data regarding the tissue 16. To create axes-specific electric fields within body 12, the patch electrodes are placed on opposed surfaces of the body 12 (e.g., chest and back, left and right sides of the thorax, and neck and leg) and form generally orthogonal x, y, and z axes. A reference electrode/patch (not shown) is typically placed near the stomach and provides a reference value and acts as the origin of the coordinate system 46 for the navigation system.

In accordance with this exemplary system 36 as depicted in FIG. 1, the patch electrodes include right side patch 44X1, left side patch 44X2, neck patch 44Y1, leg patch 44Y2, chest patch 44Z1, and back patch 44Z2; and each patch electrode is connected to a switch 48 (e.g., a multiplex switch) and a signal generator 50. The patch electrodes 44X1, 44X2 are placed along a first (x) axis; the patch electrodes 44Y1, 44Y2 are placed along a second (y) axis, and the patch electrodes 44Z1, 44Z2 are placed along a third (z) axis. Sinusoidal currents are driven through each pair of patch electrodes, and voltage measurements for one or more position sensors (e.g., ring electrodes 34 or a tip electrode located near the distal end 32 of catheter shaft 28) associated with the catheter 14 are obtained. The measured voltages are a function of the distance of the position sensors from the patch electrodes. The measured voltages are compared to the potential at the reference electrode and a position of the position sensors within the coordinate system 46 of the navigation system is determined.

The magnetic-field-based positioning system 38 in this exemplary embodiment employs magnetic fields to detect the position and orientation of the catheter 14 within the body 12. The system 38 may include the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein. In such a system, a magnetic field generator 52 may be employed having three orthogonally arranged coils (not shown) to create a magnetic field within the body 12 and to control the strength, orientation, and frequency of the field. The magnetic field generator 52 may be located above or below the patient (e.g., under a patient table) or in another appropriate location. Magnetic fields are generated by the coils and current or voltage measurements for one or more position sensors (not shown) associated with the catheter 14 are obtained. The measured currents or voltages are diminishing functions of the distance of the sensors from the coils, thereby allowing determination of a position of the sensors within a coordinate system 54 of system 38.

The display 40 is provided to convey information to a physician to assist in diagnosis and treatment. The display 40 may comprise one or more conventional computer monitors or other display devices. The display 40 may present a graphical user interface (GUI) to the physician. The GUI may include a variety of information including, for example, an image of the geometry of the tissue 16, electrophysiology data associated with the tissue 16, graphs illustrating voltage levels over time for various electrodes 34, and images of the catheter 14 and other medical devices and related information indicative of the position of the catheter 14 and other devices relative to the tissue 16.

The ECU 42 provides a means for controlling the operation of various components of the system 10, including the catheter 14, the ablation generator 22, and the switch 48 of the electric-field-based positioning system 36, and magnetic generator 52 of the magnetic-field-based positioning system 38. For example, the ECU 42 may be configured through appropriate software to provide control signals to switch 48 and thereby sequentially couple pairs of patch electrodes 44 to the signal generator 50. Excitation of each pair of electrodes 44 generates an electromagnetic field within the body 12 and within an area of interest such as the heart. The ECU 42 may also provide a means for determining the geometry of the tissue 16, electrophysiology characteristics of the tissue 16, and the position and orientation of the catheter 14 relative to tissue 16 and the body 12. The ECU 42 also provides a means for generating display signals used to control the display 40. The depicted ECU 42 represents any processing arrangement such as, for example, single device processors, multiple device processors (e.g., co-processors, master/slave processors, etc.), distributed processing across multiple components/systems, system on chip (SOC) devices, or the like.

As the catheter 14 moves within the body 12, and within the electric field generated by the electric-field-based positioning system 36, the voltage readings from the electrodes 34 change, thereby indicating the location of catheter 14 within the electric field and within the coordinate system 46 established by the system 36. The electrodes 34 communicate position signals to ECU 42 through a conventional interface (not shown).

High density catheters can be used together with a 3D mapping system and ECU 42. In some embodiments, the ECU 42 includes software and/or hardware configured to enable the high density catheters to diagnose and map rhythm disorders with accuracy, consistency, and speed. The techniques and catheters described herein enable new and better characterizations of cardiac conduction which can result in faster and more successful therapeutic procedures.

Conventional mapping techniques suffer from bipole orientation induced amplitude uncertainty and morphology variations and can suffer from activation timing variation. Slow conduction can denote cardiac tissue that is diseased or compromised and is one cause of arrhythmias. However, the present disclosure discusses removing bipole orientation uncertainty by resolving the local electric field into components aligned with the anatomy. Local electrogram signals (EGMs) reflect the local 3-D electric field produced by depolarization and may be evaluated on myocardial surfaces at regions of interest. The electronic control unit 10 can use this information to derive depolarization related normal and tangent E-fields (En and Et respectively) which are catheter orientation independent signals with reliable amplitudes, morphology/timing, and instantaneous conduction velocity vectors among other uses.

One or more of these characteristics can also enable clinicians to acquire better substrate amplitude maps and more reliable scar border delineation and characterizations of scar volume and depth. Scar tissue is known to contribute to VT and other arrhythmias. Scar depth can also influence 3-D E-fields. Deeper scar tissue can alter the derived waveforms in a manner that allows discrimination of superficial scar tissue from deep scar tissue. Also, local determinations of low amplitude and/or slow conduction velocity can help identify critical pathways for arrhythmias that are amenable to ablation therapy. In one embodiment, the electronic control unit enables more reliable EGM amplitudes and morphologies to allow better EGM reduction measures. In another embodiment, the electronic control unit enables the local assessment of conduction velocity as a critical isthmus in the tissue or a lesion gap is approached. The electronic control unit also enables characterizations of ablation lesions from En and Et before, during, and after ablation to help determine the growth and effectiveness of any lesions that have been formed.

Local electrophysiologic propagation information may also be determined by pacing with such a catheter and observing the resulting spread of depolarization from immediately adjacent to the site where capture occurs. This is difficult currently and the directional information as described in this disclosure may serve as a clue to anatomic or functional conduction blocks. Even without pacing, conduction around obstacles such as valve orifices or blocks is known to become curved and slowed and this may be detected and directly mapped in some embodiments. The electronic control unit can also allow for more consistent substrate amplitude maps that can show activation direction and conduction velocity.

Embodiments of this disclosure employ closely spaced electrodes in spatial arrangements that can be used to derive an approximate local electric field (E-field) on an endocardial or epicardial surface and in so doing derive useful measures of conduction that are insensitive to catheter orientation. Although EP catheters in the hands of skilled operators can be placed in almost any location, it is often the case that achievable catheter orientations are few. This lack of achievable orientations can limit the data that can be collected by the catheters. The catheters and mapping system described in this disclosure use additional (i.e., segmented) electrodes to determine properties of myocardium by putting information into its proper 2-D and 3-D spatial and temporal contexts.

In addition to enhanced maps from multi-electrode diagnostic catheters, embodiments also contemplate the use of ablation catheters with these same or similar advantages. The result is an expanded and catheter orientation independent set of local electrophysiologic information such as: normal EGM amplitude, tangent EGM amplitude and direction, tangent EGM eccentricity, 2-D and 3-D E-Field amplitude, activation times derived from signals of reliable morphology, and conduction velocity magnitude and direction. One or more such measures can prove valuable when applied to a diagnostic catheter and even more so when applied to a catheter that will also deliver ablation energy during an EP procedure.

Figure 2:
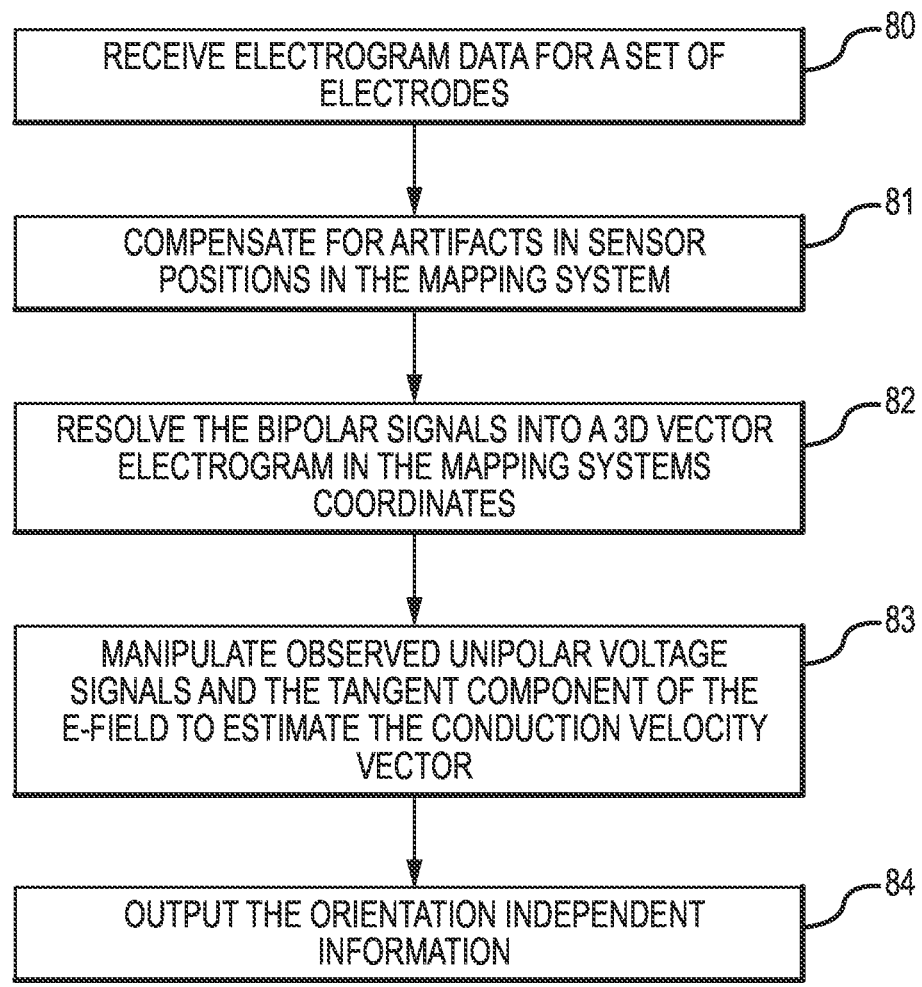
FIG. 2 is a flow chart associated with a method for determining electrophysiological data, in accordance with embodiments of the present disclosure.

There are at least three steps that can be performed by the electronic control system to extract orientation independent information from closely spaced multi-electrode catheters in an electrical mapping environment. The three steps are illustrated in FIG. 2. After receiving electrogram data for a set of electrodes 80, the first step is to compensate for artifacts in sensor positions in the mapping system; a situation which can be common in segmented electrode catheters located by electric-field-based positioning systems 81. The second step is to resolve the bipolar signals into a 3D vector electrogram in the mapping system's coordinates, with a component normal to the cardiac surface and another tangent to the surface 82. In a separate embodiment, planar electrode bipolar signals can be resolved into a 2D vector electrogram in the mapping system's coordinates that is tangent to the cardiac surface. The third step, performed if local conduction velocity is of interest, is to manipulate observed unipolar voltage signals and the tangent component of the vector E-field to arrive at a valid local estimate of the conduction velocity vector 83 on a beat-by-beat basis similar to that available today for peak-to-peak amplitude or local activation time. The electronic control system can then output the orientation independent information to a user, a display, or other device 84. The first 2 or all 3 steps may be done with catheters or other medical devices that include segmented or more conventional electrodes. A segmented electrode is one which does not extend around the entire circumference of a catheter. Multiple segmented electrodes can extend around a circumference of a catheter at the same position along a longitudinal axis of the catheter. Further, segmented electrodes can comprise electrodes that are often smaller and distributed in proximity to one another. They may sometimes resemble split or "segmented" conventional electrodes and need to be placed appropriately on the catheter to determine properties of myocardium by putting information into its proper 2-D and 3-D spatial and temporal contexts. This can be seen, for example, as segmented electrodes 121, 122, and 123 in FIG. 3A.

Figure 3A:
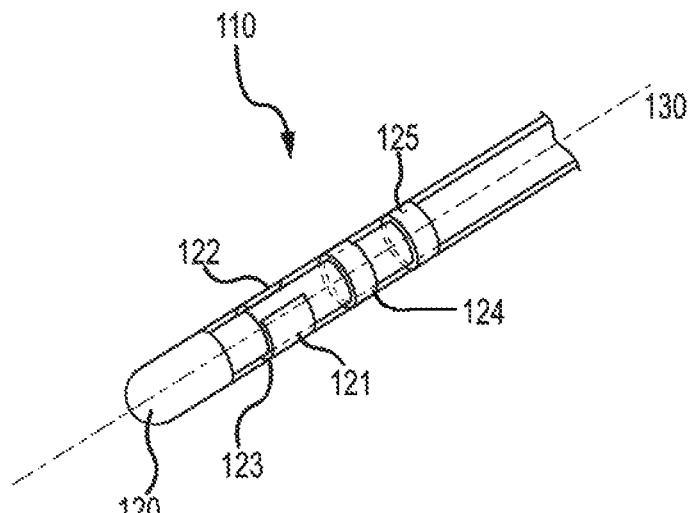
FIGS. 3A and 3B are isometric and side views of an ablation catheter with a tip electrode, a segmented ring electrode and several regular ring electrodes.
Figure 3B:
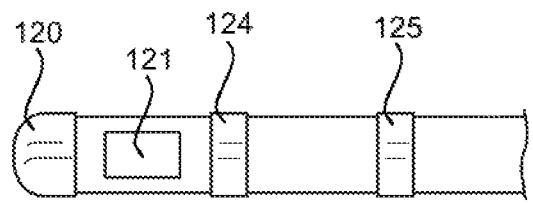
Figure 3C:
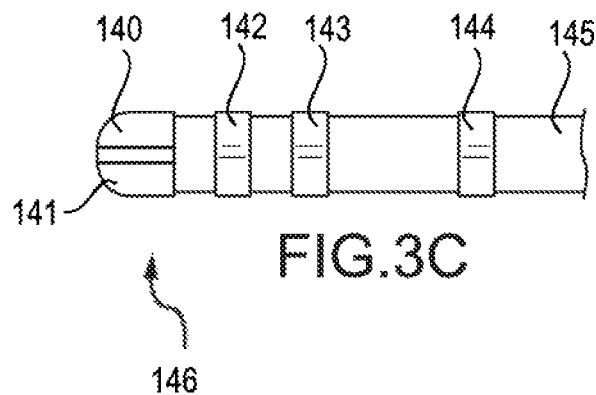
FIGS. 3C and 3D are isometric and side views of an ablation catheter with a segmented tip electrode and several regular ring electrodes.
Figure 3D:
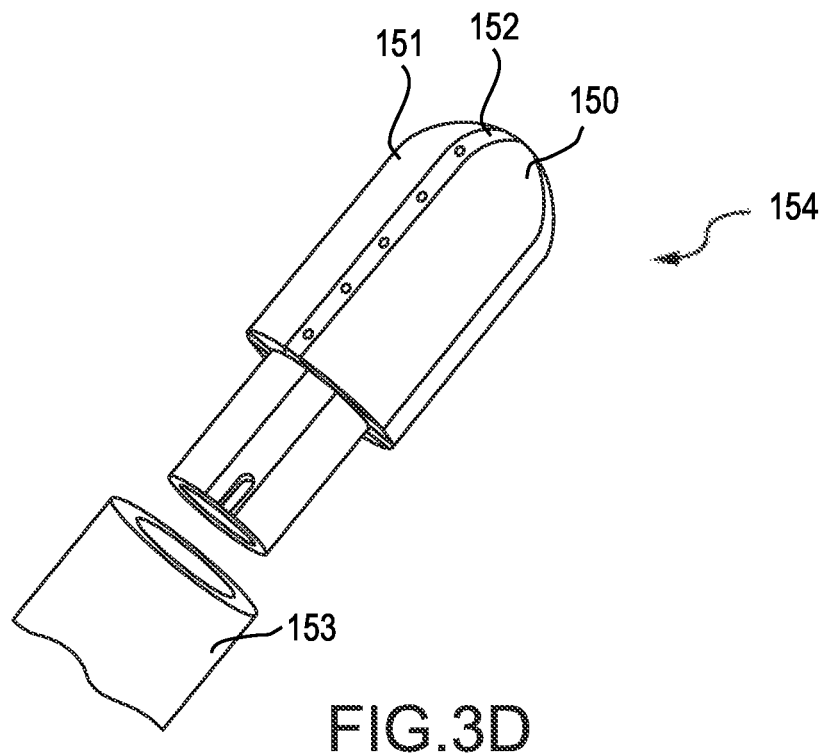
Figure 3E:
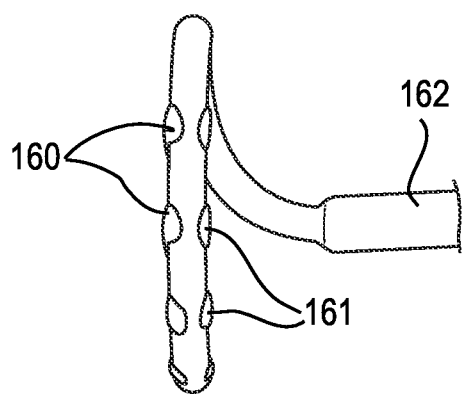
FIG. 3E is a side view of a diagnostic catheter with opposing electrodes.

FIGS. 3A and 3B are isometric and side views of an example ablation catheter 110 with a segmented ring electrode and several more conventional ring electrodes. As shown in FIG. 3A, the catheter 110 has a tip electrode 120 which can be suitable for RF ablation, a first, second, and third split ring or segmented electrode 121, 122, 123, and one or more circumferential ring electrodes 124, 125. The segmented electrodes can be utilized in conjunction with adjacent tip and/or ring electrodes to permit one or more 3-D determinations of the local E-field as depolarization occurs. However, other catheters with segmented electrodes can also use the procedures set forth within. Several examples of catheters with segmented electrodes include U.S. Patent Publication No. 2010/0168560 titled "Devices and Methods For Catheter Location," and U.S. Patent Publication No. 2010/0168557 titled "Multi-Electrode Ablation Sensing Catheter and System," both of which are hereby incorporated by reference as though fully set forth herein. FIGS. 3C and 3D show side and isometric views of alternative ablation catheters having a segmented tip configuration which can be used to obtain orientation independent information. FIG. 3C is a side view of another embodiment of an ablation catheter 145 with a segmented tip assembly 146. The ablation catheter 145 comprises first, second, and third ring electrodes 142, 143, 144 and a segmented tip assembly 146 that is divided into at least two electrodes. In the illustrated example a first segmented tip electrode 140 and a second segmented tip electrode 141 are illustrated. FIG. 3D depicts an isometric view of another embodiment of a segmented tip assembly 154 and a catheter body 153. The segmented tip assembly 154 comprises a first segmented tip segment 150, a second segmented tip electrode 151, and an electrically non-conductive area 152 between the first and second segmented tip electrodes. In other embodiments the segmented tip electrode can comprise four discrete segmented tip electrodes and an electrically non-conductive area surrounding each segmented tip electrode. FIG. 3E illustrates a side view of a diagnostic catheter with opposing electrodes suitable for 2-D determinations of the local E-field. The catheter illustrated in FIG. 3E comprises a catheter body 162, and a plurality of segmented electrodes around a circular, or lasso, catheter tip. The catheter comprises a first plurality of segmented electrodes 160 that face distally on the circular catheter, and a second plurality of segmented electrodes 161 that faces proximally on the circular catheter. The number and spacing between the segmented electrodes in both the first and second plurality of segmented electrodes 160, 161 can vary in different embodiments. In some embodiments only the first plurality of segmented electrodes 160 or the second plurality of segmented electrodes 161 can be present on the circular catheter.

Figure 4A:
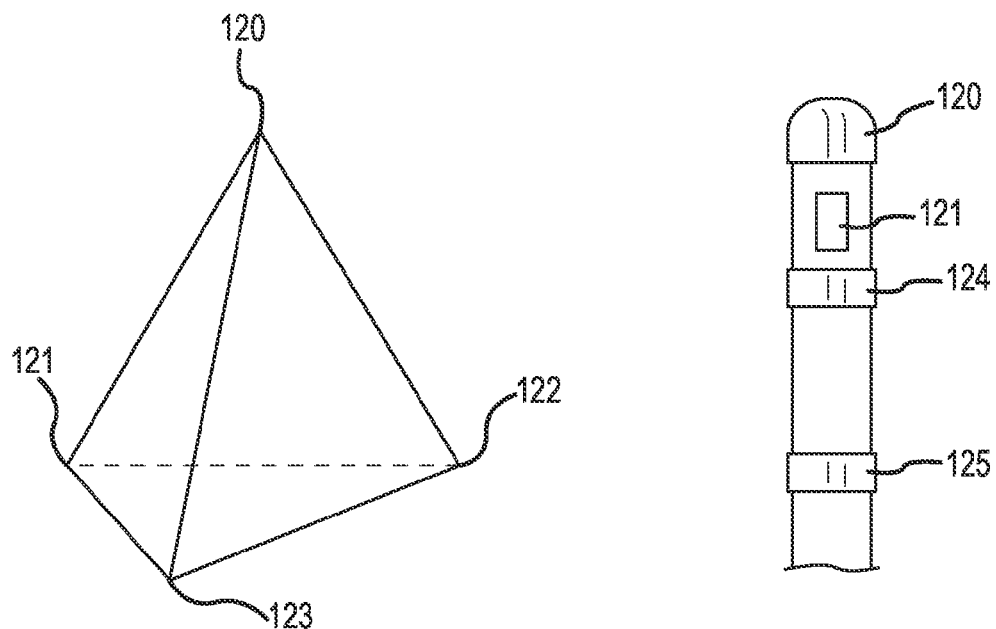
FIG. 4A is an isometric view of the distal tetrahedron along with the corresponding side view of the segmented ring ablation catheter.
Figure 4B:
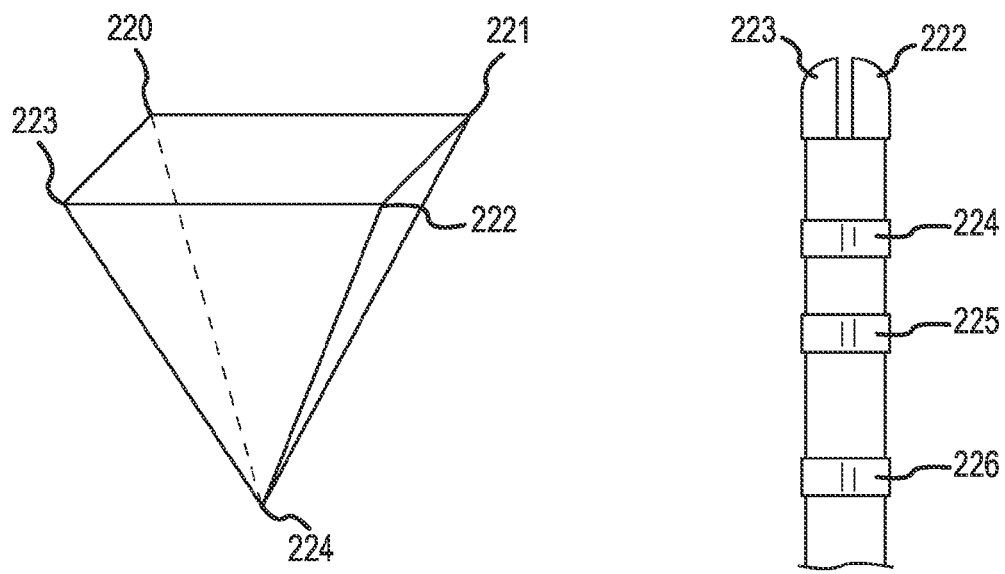
FIG. 4B is an isometric view of the distal pyramid along with the corresponding side view of the segmented tip ablation catheter.

The illustrations of FIGS. 4A and 4B show the two exemplary ablation catheter designs paired up with a tetrahedron and inverted pyramid. The catheter of FIGS. 3A and 3B is represented by the tetrahedron of FIG. 4A. The tip electrode 120 is shown in relation to the split ring electrodes 121, 122, and 123. The position coordinates of these electrodes are denoted D, 2, 3, and 4 respectively. Similarly, the catheter of FIGS. 3C and 3D is represented by the inverted pyramid of FIG. 4B. The catheter of FIG. 4B further comprises a first ring electrode 224, a second ring electrode 225, and a third ring electrode 226. The four tip electrodes 220, 221, 222, and 223 are shown in relation to the adjacent first ring electrode 224. The position coordinates of these electrodes are denoted D, 2, 3, 4, and 5 respectively.

The first step to extracting orientation independent information entails a further aspect of this disclosure, the compensation for electrode impedance location and navigational artifacts that may be prominent with small electrodes, particularly those that are split or segmented on the surface of a catheter shaft. Constraints of physical construction, scaling error, and non-ideal electrode/amplifier impedance characteristics are combined to estimate a more realistic electrode spatial distribution with the result that suitable local E-field determinations may be made as well as more reliable and catheter orientation independent clinical assessments.

Impedance localization artifacts can arise from a variety of sources. A high electrode impedance coupling to the body's conductive medium is an artifact that disturbs electrode positions in a characteristic manner. These electrodes are displaced toward the external reference electrode, which is typically around 200-400 mm inferior to the heart. As little as a 1% deviation in this manner thus produces a 2-4 mm shift. The extent of such a shift depends on a variety of factors, including: other electrode impedances, electrode surface area, measured impedance, electrode surface contaminants, and tissue contact, among others. Other instances of known shift and drift, and apparatus and methods to correct are disclosed in U.S. patent application Ser. No. 13/690,737, filed 30 Nov. 2012, and hereby incorporated by reference as through fully set forth herein. These factors are only partly known ahead of time. Correction of this artifact can thus be helped by referring to other electrodes on the catheter and by knowledge of its physical construction. In one example, the other electrodes being referred to are larger electrodes or circumferential electrodes and are thus less susceptible to this type of deviation. Alternatively, larger electrodes may be adjusted in such a manner as to position them properly with respect to the segmented electrodes. Since this effect can be dominant and is systematic, it can be compensated, for example, by introducing a multiplicative correction factor. In one example, a factor in the vicinity of 1.002-1.010 is selected and is conditioned on bringing the affected segmented electrodes to approximately the correct location with respect to the other conventional electrodes. Conversely a factor of 0.990-0.998 may bring conventional electrodes to a correct location relative to the segmented electrodes.

The electronic control unit can compensate for impedance localization artifacts by the following general steps. The steps in this specific embodiment can be used to compensate for smaller or segmented electrodes on a catheter that also includes ring electrodes as currently known in the art. The following steps detail how the electronic control unit can be used, in some embodiments, to compensate for position artifacts with the catheter shown in FIGS. 3A, 3B, and 4A. First, the measured coordinates of the large circumferential ring electrodes 124, 125 and the tip electrode 120 are used to fit a line and thereby determine the catheter's distal longitudinal axis. The observed locations of electrodes 120, 124 and 125 (denoted D, 5, and 6 in FIG. 7) are then adjusted to lie on this axis by determining the locations on the axis closest to their measured coordinates (denoted $D_\Delta$, $5_\Delta$, and $6_\Delta$ in FIG. 8). The electronic control unit can then denote the resulting best fit axis A 130 and the best guess for the tip and ring electrodes 120, 124, 125 with coordinates denoted $D_\Delta$, $5_\Delta$, and $6_\Delta$ in FIG. 8. Another method of estimating the spatial orientation of a catheter in a mapping system is disclosed in U.S. patent application Ser. No. 12/347,271, filed 31 Dec. 2008, and hereby incorporated by reference as though fully set forth herein.

In some embodiments, the mapping system can next compute from the electronic control unit's measured and physical distances ($d_{measured}$ and $d_{physical}$) between the tip electrode 120 and the first ring electrode 124, and the first ring electrode 124 and the second ring electrode 125 a global (i.e., location and direction independent) scale factor s such that $s*d_{physical}=d_{measured}$.

The electronic control unit then computes the centroid of the first, second, and third segmented ring electrodes 121, 122, 123 from the measured coordinates denoted 2, 3, and 4 in FIG. 7 and denotes this location as $C_M$ (not shown). The next step can include using the physical proportion of the distance between the tip electrode 120 and the first ring electrode 124, and assigning an equivalent location on the best fit line for the centroid of the first, second, and third segmented electrodes 121, 122, 123 and denoting this location $C_A$ (not shown). The electronic control unit uses the discrepancy between $C_M$ and $C_A$ to determine impedance scale factor zs>1 (e.g. 1.002-1.010 as described above) that puts $zs*C_M$ as close to $C_A$ as possible. This results in a best correction for small electrodes and impedance increases compared to traditional electrodes. In the exemplary embodiment of FIGS. 3A and 3B the traditional electrodes comprise the tip electrode 120, the first ring electrode 124, and the second ring electrode 125.

The electronic control unit can next expand the measured first, second, and third segmented electrode 121, 122, 123 coordinates by zs so they now lie between the tip electrode 120 and the first ring electrode 124. This step introduces electrode impedance compensation, a dominant source of electrode position error. The extent of compensation for the electrodes can vary with factors such as surface area and tissue contact, among others.

The electronic control unit can next project along the axis A 130 the resulting compensated first, second, and third segmented electrode 121, 122, 123 coordinates onto a plane $P_A$ that passes through $C_A$ and is perpendicular to the best fit axis A 130, and translate the coordinates of the first, second, and third segmented electrodes 121, 122, 123 so that their centroid lies at $C_A$ in the plane $P_A$. With the exception of lesser (second order) distortions that lie in and out of plane $P_A$, the first, second, and third segmented electrode 121, 122, 123 coordinates are now at their best fit locations. In one embodiment the electrodes of the catheter illustrated in FIGS. 3A and 3B form two tetrahedra. The first tetrahedron comprises the tip electrode 120 and the first, second, and third segmented electrodes 121, 122, 123. The second tetrahedron comprises the first ring electrode 124 and the first, second, and third segmented electrodes 121, 122, 123. FIG. 4A illustrates the distal tetrahedron of the catheter formed by the tip electrode 120 and the first, second, and third segmented electrodes 121, 122, 123.

As a possible additional step, the electronic control unit can construct an equilateral triangle with split ring electrodes at its vertices, centered at $C_A$ with sides that have the length of scale factors times the distance between electrodes 121, 122, and 123, and find the angle of rotation about $C_A$ in plane $P_A$ that minimizes the sum-squared distance between corresponding electrodes/vertices. This result allows the electronic control unit to have best fit positions for all of the electrodes from the tip electrode 120 to the first ring electrode 124 which correspond to coordinates $D_\Delta$, $2_\Delta$, $3_\Delta$, $4_\Delta$, and $5_\Delta$ of FIG. 8. The electronic control unit can now proceed to resolve local EP information.

The compensation step for electrode impedance location and navigational artifacts can introduce knowledge of segmented electrode positions, an estimate of segment electrode scaling error obtained from large conventional electrode spacing, and the measured coordinates of the segmented electrodes. Software in the ECU 42 or other device employing parameters specific to a segmented catheter design can be used to determine the correct compensation. Alternatively or in addition, systematic artifacts that result from proximity of the electrode to an insulated catheter shaft may be modeled and corrected. In one embodiment, measured electrode positions, modeled in electric field software such as Coulomb, sold by INTEGRATED Engineering Software, can be predictably altered and the measured positions can then be adjusted based on displacements predicted by the model.

The second step to extracting orientation independent information entails deriving an E-field from the observed bipolar signals, by considering the E-field to be projected onto bipole vectors which typically form a non-orthogonal set of basis vectors. From this set of basis vectors the E-field is then expressed in orthonormal mapping system coordinates. The surface geometry and the catheter's location then yield a unit vector that is the local surface normal, also referred to as n-hat or n̂. A 3D vector E-field E=En+Et can then be decomposed by the electronic control unit into a component aligned with the surface normal denoted En and the remainder which lies in a 2D subspace tangent to the surface which is denoted Et.

Catheters with high density arrays of electrodes which can be maneuvered into lying along a surface offer a 2D variant of this process. After compensating for mapping system artifacts by some or all the techniques outlined above, cells or cliques are composed of the three or four neighboring electrodes on 2 splines or arms that are closest to each other. In one embodiment, these cliques form rectangular elements with dimensions roughly 2×3 mm. The resulting possible bipolar signals (of which only 3 are linearly independent) over determine the local 2D tangent E-field. Using a pseudo-inverse form of linear algebra, these signals are converted to best fit coefficients for an orthonormal basis which is Et in the mapping system coordinates. Again, catheter orientation independent amplitude and more consistent timing measures can be derived as well as local conduction velocity vector determination described below.

In one embodiment, as seen in FIG. 3A. a catheter has a plurality of electrodes that form two tetrahedra when lines are drawn between adjacent electrodes. The tetrahedra formed between the electrodes in the catheter shown in FIG. 3A is illustrated in FIG. 4. When a catheter such as that seen in FIG. 3A comprises electrodes that form two tetrahedra then the 3 (x,y,z) mapping system coordinates of the 4 electrodes for each of the two tetrahedra may be placed into 3×4 matrices. The mapping system can then denote one of these tetrahedra by coordinate matrix X. After choosing one vertex as a reference (e.g. D), the electronic control unit computes vertex displacements dX from D to each remaining vertex by pairwise subtraction using X and captures this operation in matrix notation as dX=X·F where F is the appropriate 4×3 pairwise subtraction matrix comprised of 0, +1, and −1's. As it is non-degenerate, dX is an invertible 3×3 matrix.

The electronic control unit then lets E stand for the local electric field in the mapping system coordinate frame. As dX was determined from the mapping system coordinates in a navigational electric field, the same effects are present for electrogram signals. In this embodiment phi or $\phi$ is a 4×1 vector of unipolar electric potentials at each of the electrodes of the tetrahedron. Similarly the electronic control unit can define the corresponding 3×1 vector of bipole signals $d\phi = F^T \cdot \phi$ and relates the local electric field to the 3 measured bipole potentials $d\phi$ by $$d\phi = -(dX)^T \cdot E$$

And as a result the electronic control unit determines the value of E from measured quantities X and $\phi$ by calculating:

$$E = -(dX)^T)^{-1} d\phi = -(dX)^{-T} \cdot F^T \cdot \phi$$

In the case of an ablation catheter embodiment such as shown in FIGS. 3C, 3D, and 4B the overdetermined electric field E may be best fit to the observed bipole potentials $d\phi$ by using a pseudo-inverse as in $$E = -((dX)^T)^+ \cdot d\phi = -((dX)^T)^+ \cdot F^T \cdot \phi$$

This is the local E field in the mapping system body coordinates derived from measured bipoles or unipoles and electrode coordinates. The electronic control unit can sample data from the electrodes at various frequencies. Unipolar voltages $\phi$ change rapidly with time whereas the electrode coordinates and thus dX change much more slowly. In one embodiment, $\phi$ can be sampled by the electronic control unit at 2034 Hz while the electrode coordinates can be sampled at 102 Hz and can be filtered to under 1 Hz. The above sampling rates are only one example of the frequencies that can be used by the system or ECU. The sampling rates of the electronic control unit can be any that allow for proper location and data collection to occur.

Figure 6:
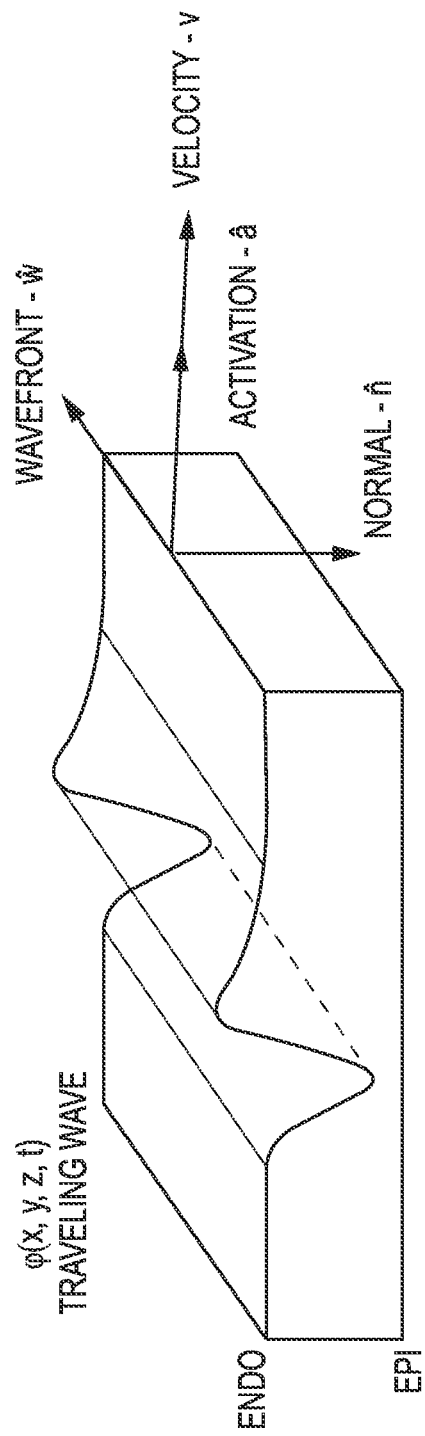
FIG. 6 is a diagrammatic view of a traveling depolarization wave along with the unit vector directions.
Figure 12:
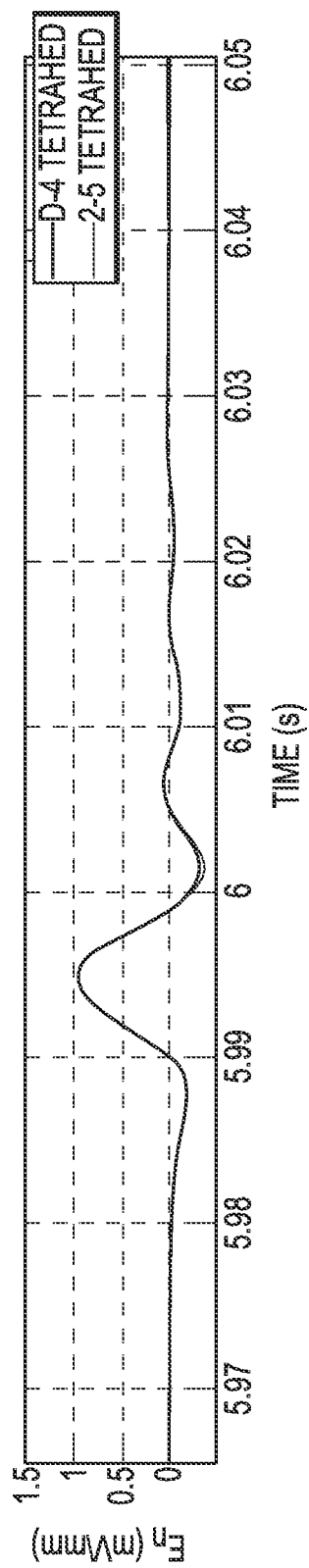

Conduction velocity magnitude and direction can be determined in a novel manner over a single beat from a system of a few closely spaced electrodes capable of resolving the local tangent E-field (Et) and measuring the local unipolar voltage. Locally, if the depolarization wavefront passes the catheter electrodes as a planar front progressing uniformly in a homogenous medium, then orthogonal unit vectors a-hat (â) and w-hat (ŵ) can be defined in the tangent plane. FIG. 6 illustrates a homogenous depolarization wavefront travelling from left to right on the endocardial surface. â is defined as the direction along which the wavefront is propagating (also the direction of conduction velocity) and ŵ is parallel to the wavefront. â should also be aligned with the direction along which maximum voltage swings are expected for Et. The component of Et along â is defined as Ea. So $$E_t = E_a \hat{a} + E_w \hat{w} = E_a \hat{a}$$

since under the assumption of a homogenous, uniformly travelling depolarization wavefront Ew is identically zero.

Recognizing that the potential field $\phi$ is a function of space and time, $\phi(x, y, z, t)$, the total derivative of $\phi$ can be defined as $$\frac{D\varphi}{Dt} = \frac{\partial \varphi}{\partial t} + \frac{\partial \varphi}{\partial x}\frac{dx}{dt} + \frac{\partial \varphi}{\partial y}\frac{dy}{dt} + \frac{\partial \varphi}{\partial z}\frac{dz}{dt}$$

The total derivative is the rate of change of potential observed when moving along with the depolarization wave. Under assumptions of uniform and homogenous cardiac conduction locally, the total derivative is zero.

$$\frac{D\varphi}{Dt} = \dot{\varphi} + v \cdot \nabla\varphi = 0$$

where v is the conduction velocity vector. Recognizing that $E = -\nabla\phi$ and that only the component of E-field in the tangent plane contributes to the inner product, we get $$E_t \cdot v = \dot{\phi} \text{ so that } E_a(\hat{a} \cdot v) = \dot{\phi}.$$

The conduction velocity vector v can then expressed as $$v = \frac{\dot{\varphi}}{E_a} \hat{a}$$

Although the expression above holds in principle at every time point, when isoelectric or when signal levels are sufficiently small, the ratio of $\dot{\phi}$ to $E_a$ cannot be meaningfully determined. The evaluation only holds for the approximately 10-20 ms during depolarization of the substrate underneath the catheter.

An alternate way to derive and explain the conduction velocity described in the equation above is presented next. In the idealized case of a wavefront traveling at uniform velocity and direction on an endocardial surface, the surface can be parameterized by variables r and s in an orthonormal fashion and the 2D position vector $p=(p_r, p_s)$. In this example, x, y, or z are avoided as they are reserved for the mapping system coordinates. To ensure the wavefront in this example is idealized and local, several assumptions are made: the distribution of potential is unchanged (static) except for translation in time, the translation in time occurs with a uniform velocity vector $v=(v_r, v_s)$, and the static distribution of potential is continuously differentiable and varies only in the direction of v (in the plane r-s). The assumption that the static distribution of potential varies only along v comes from an inability to distinguish an inclined wavefront moving at velocity v from a wavefront that is not inclined (is perpendicular to v) moving at another velocity.

At time $t_0$ a unipolar endocardial voltage distribution $\phi(r, s, t_0)$ or $\phi(p, t_0)$ is present. When the electronic control unit uses the idealized assumption of a uniform travelling wave, at some time $t>t_0$ the voltage distribution is simply translated in space from its earlier distribution $$\phi(r,s,t)=\phi(p,t)=\phi(p-(v\cdot(t-t_0)),t_0)$$

where $v=(v_r, v_s)$ is the wavefront velocity vector in coordinate frame r-s which is tangent to the local endocardial surface. A convenient shorthand is to consider a static (time invariant) wave distribution to be $u(r, s)$. Then the travelling wave is the static distribution $u(r,s)$ translated in a time-dependent manner.

$$u(r(t),s(t))=u(p-v\cdot(t-t_0))=\phi(p,t)$$

The equation above relates the time varying voltage at point p to 2-D conduction velocity vector v through static potential distribution u.

Figure 5:
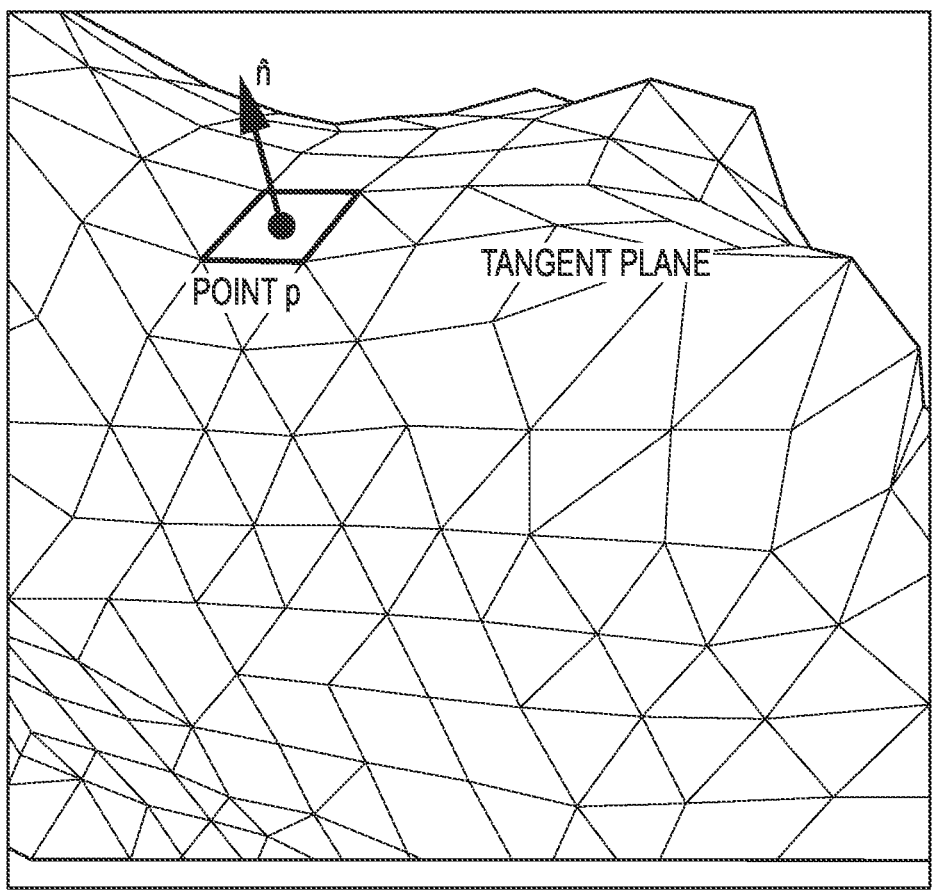
FIG. 5 is a diagrammatic view of the surface anatomy near a point of interest and the unit surface normal.

From a collection of four closely spaced non-coplanar electrodes around point p on the surface of the heart, the electronic control unit can directly obtain the four time varying unipolar voltages. This allows the electronic control unit to estimate various EP properties of point p. Surface point p has unit normal n̂ and tangent plane as shown in FIG. 5.

The electronic control unit begins with the physics of a scalar potential field and the segmented catheter electrode array. The time varying voltage $\phi(t)$ at point p can be estimated from the mean of the observed electrodes. The time varying local electric field $E(t)=-\nabla\phi(t)$ may also be estimated from an appropriate transformation of three or more bipole signals. This can be used to resolve coordinate frames and electrode spacing.

Wavefront conduction velocity, a catheter orientation independent property of the substrate and conduction system, can be derived tangent to the surface at point p. An example of the wavefront is illustrated in FIG. 6. Wavefront conduction velocity v can be used by an electrophysiologist and is generally difficult or time consuming to determine using traditional techniques. The electronic control unit can then take the total derivative of v with respect to t, hoping to recognize measureable quantities and be able to solve for v. Starting from the equation that relates u and $\phi$ above, $$\dot{\phi} = \frac{d\phi}{dt} = \frac{\partial u}{\partial r}\frac{dr}{dt} + \frac{\partial u}{\partial s}\frac{ds}{dt} = -\nabla u \cdot v$$

This follows from what is meant by dr/dt and ds/dt in the total derivative expression above and that $$\frac{dr}{dt} = \frac{d}{dt}(p_r - v_r(t-t_0)) = -v_r$$

$$\frac{ds}{dt} = \frac{d}{dt}(p_s - v_s(t-t_0)) = -v_s$$

The electronic control unit can next consider the vector electric field at point p to be composed of normal and tangent components. By having $E_n$ be the 3D vector normal component in the direction of unit vector n̂, the electronic control unit can define the tangent component $E_t$ to be $$E_t=E-E_n=-\nabla u$$

The electronic control unit can represent $E_t$ also as a 2D vector in (r,s) coordinates, where it is the gradient of the local potential field on the endocardial surface which can be identified as $-\nabla u$. The key result is that $$\dot{\phi}=E_t\cdot v$$

The electronic control unit can then obtain a properly directed estimate of wavefront velocity at point p from observable quantities by the following and recognizing that $E_t=E_a\hat{a}$:

$$v = \frac{\dot{\phi}}{\|E_t\|} \cdot \frac{E_t}{\|E_t\|} = \frac{\dot{\phi}}{E_a}\hat{a}$$

This is the same result for conduction velocity as derived above.

Figure 13:
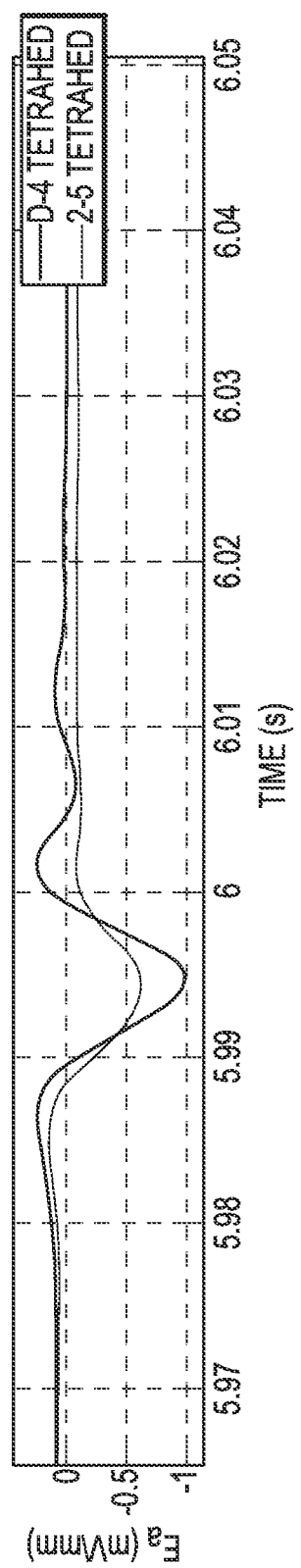

FIGS. 9-13 illustrates electrode unipole signals from each of the electrodes in the catheter seen in FIG. 3A as determined by the mapping system and denoted as phi ($\phi$). In the illustrated embodiment the unipole signals possess typical unipolar morphology (FIG. 9). From each phi, its time derivative phi-dot ($\dot{\phi}$) is computed and plotted by the mapping system (FIG. 10). If the determined unipoles, phi, are mainly negative going single phase pulses, then phi-dots are mainly biphasic with a negative going phase followed by a positive phase. Both waveforms for En, shown in FIG. 12, from the proximal and distal tetrahedra are consistent and reveal a single phase positive waveform of peak-to-peak amplitude 1.4 mV. The Ea signals in FIG. 13 are also consistent across the proximal and distal tetrahedra. FIG. 11 illustrates the conduction velocity magnitude estimated by taking the instantaneous ratio of $\dot{\phi}$ to Ea, which is seen to be approximately 1 mm/ms.

Figure 14:
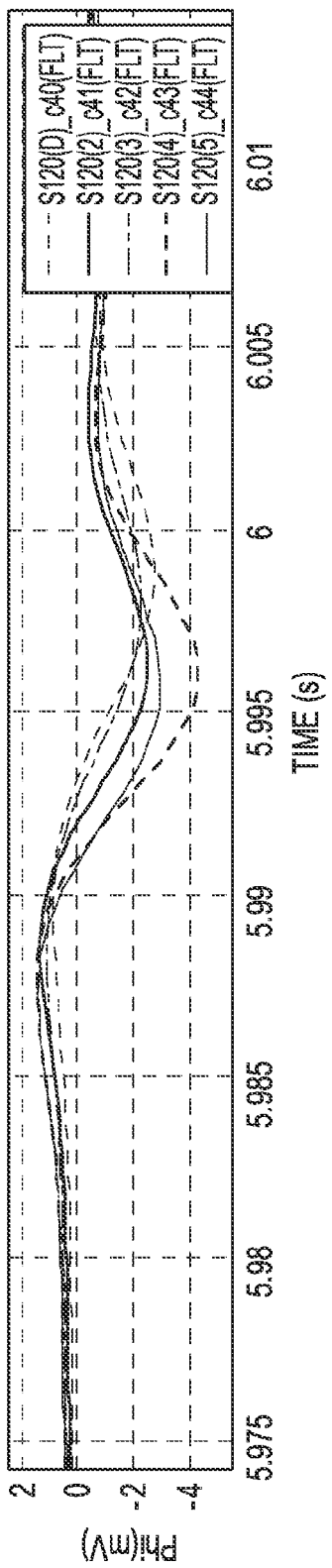
FIGS. 14-15, 16-17, and 18-19 are plots of three consecutive beats featuring expanded views of EP signals derived from the five distal most electrodes on the catheter of FIGS. 2A and 2B.
Figure 15:
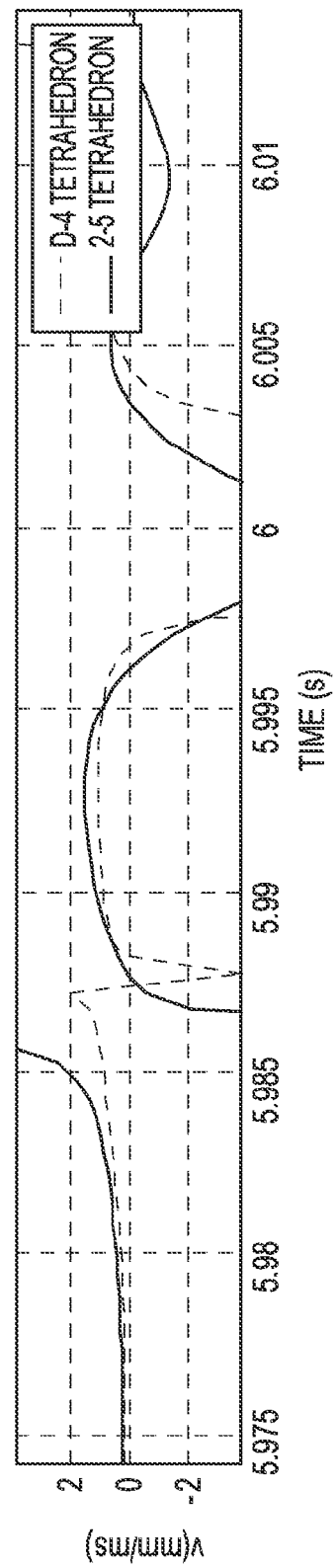
Figure 16:
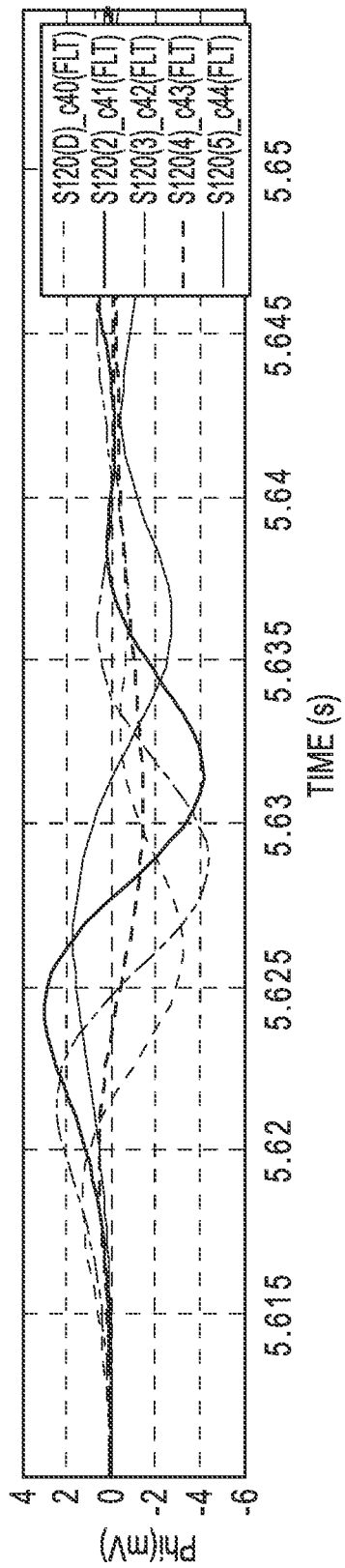
Figure 17:
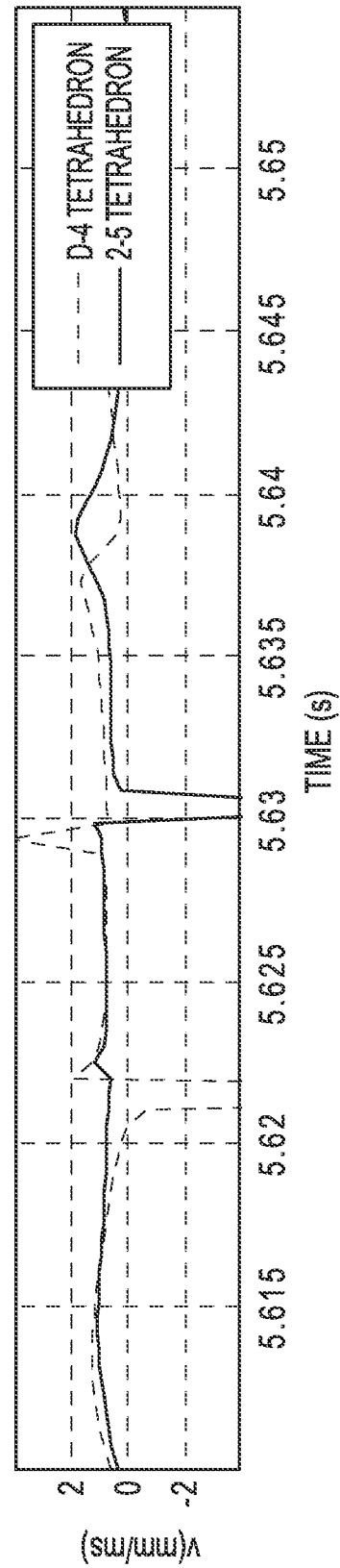
Figure 18:
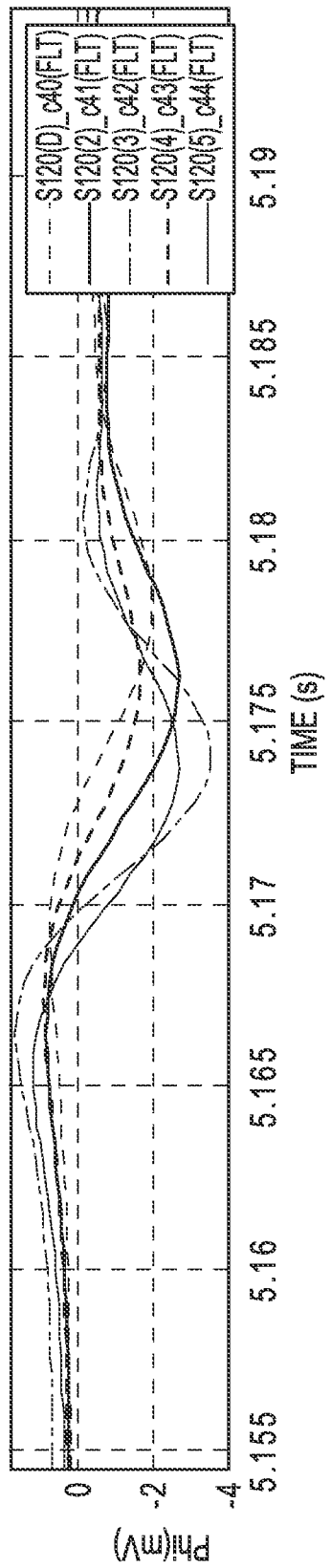
Figure 19:
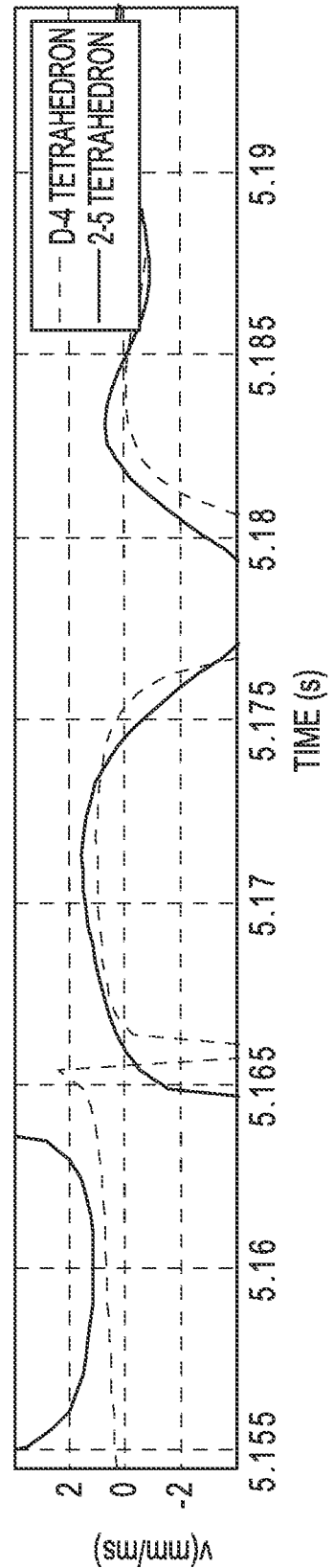
Figure 20:
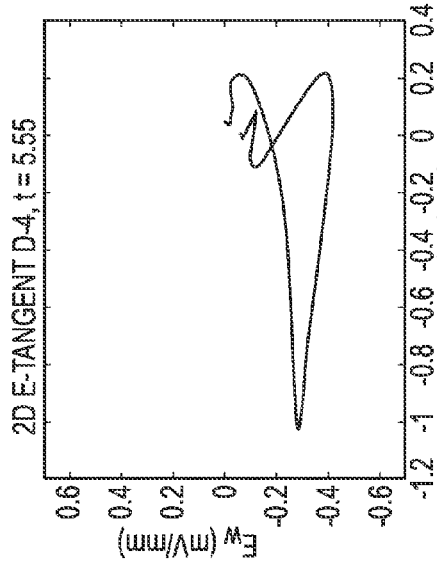
FIGS. 20-23 are plots of EP signal Et in its tangent plane for four consecutive cardiac cycles.
Figure 21:
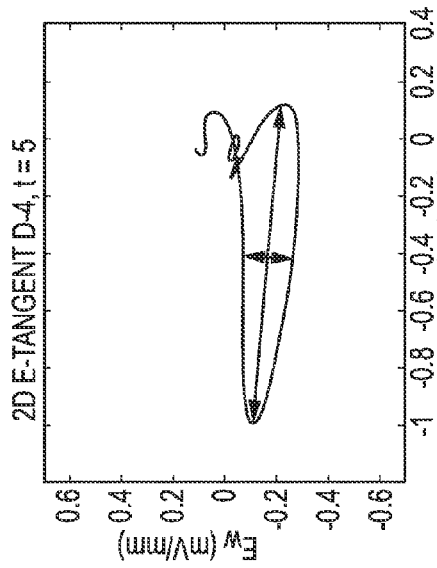
Figure 22:
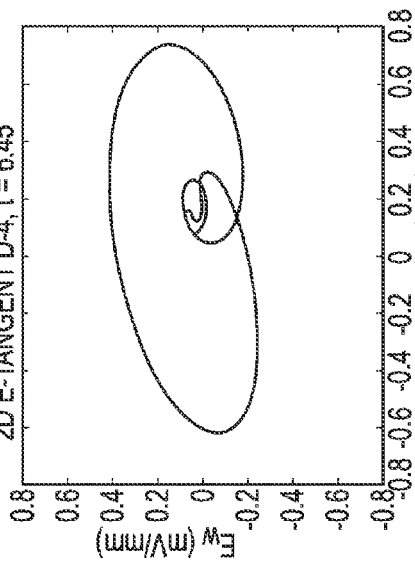
Figure 23:
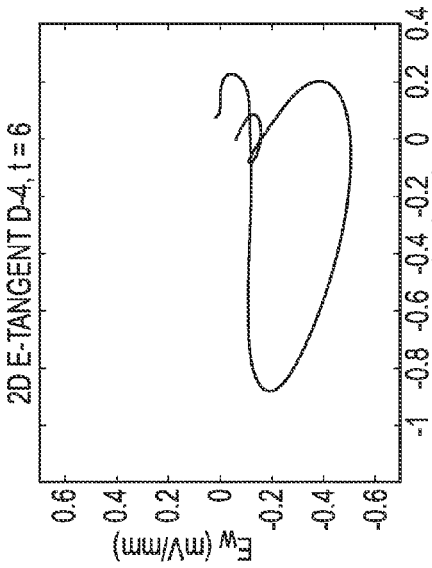

FIGS. 14-19 illustrate further mapping system recordings of unipolar signals and derived conduction velocity magnitudes. FIGS. 14-19 illustrate three pairs of recordings with FIGS. 14 and 15 plotting a first recording, FIGS. 16 and 17 plotting a second recording, and FIGS. 18 and 19 plotting a third recording. The conduction velocity magnitudes in these figures were approximately 1 mm/ms.

If the wavefront passes the catheter electrodes as a planar front progressing uniformly in a homogeneous medium, then Et should consist of voltage swings along a single dominant axis—aligned with the direction of propagation (â). As illustrated in FIGS. 20-23 looking at Et in its plane with the horizontal +x direction chosen to be along â, there is around 3-8 times more signal along x than y. This signal indicates that, at least locally, planar wavefronts pass by as if conducted in a fairly homogeneous medium. The eccentricity of these loops can be assessed and can indicate non-uniform local conduction which may be of clinical interest.

The systems described by this disclosure are intended to provide catheter orientation-independent characterization of cardiac conduction that would enable an electrophysiologist to diagnose disorders and deliver therapy. Typically this would be realized using a multi-electrode catheter that would be used in conjunction with the system's algorithms and along with an amplifier for measuring electrograms, electrode locations, and orientations.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of all embodiments.

Reference throughout the specification to "various embodiments," "some embodiments," "one embodiment," or "an embodiment," or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial or directional terms such as "vertical," "horizontal," "up," "down," "clockwise," and "counter-clockwise" may be used herein with respect to the illustrated embodiments. However, medical instruments may be used in many orientations and positions, and these terms are not intended to be limiting and absolute. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for determining electrophysiological data, comprising:
    an electronic control unit configured to:
        receive electrogram data for a set of electrodes,
        compose a clique of at least three neighboring electrodes from the set of electrodes, wherein the electrogram data comprises a plurality of bipole signals taken between the at least three neighboring electrodes in the clique;
        receive position and orientation information for the set of electrodes from a mapping system;
        derive an E-field from the plurality of bipole signals of the clique, wherein bipole signals taken between the at least three neighboring electrodes in the clique overdetermine the E-field;
        determine catheter orientation independent information of a tissue based on the electrogram data and position and orientation information from the set of electrodes, wherein the catheter orientation independent information comprises a local tangent E-field and an orthogonal unit vector in the direction along which a wavefront is propagating (a); and
        output the orientation independent information to a user or process.

2. The system according to claim 1, wherein the orientation independent information further comprises at least one of a 2D vector electric field, a 3D vector electric field, a normal electric field, the eccentricity of the tangent electric field loop, derived normal and tangent bipolar electrogram signals, a wavefront conduction velocity, or a unit direction vector.

3. The system according to claim 1, wherein the electronic control unit is further configured to compensate for artifacts in the position and orientation information received from the mapping system.

4. The system according to claim 1, wherein the electronic control unit is further configured to resolve the electrogram data into a 3D vector electrogram in a coordinate system of the mapping system.

5. The system according to claim 1, wherein the catheter orientation independent information further comprises a wavefront conduction velocity and a 2D vector electric field.

6. The system according to claim 1, wherein the electronic control unit is further configured to resolve the electrogram data into a 2D vector electrogram in a coordinate system of the mapping system.

7. The system according to claim 6, wherein the catheter orientation independent information further comprises a conduction velocity magnitude.

8. The system according to claim 1, wherein the orientation independent information further comprises a single phase positive waveform.

9. The system according to claim 1, wherein the orientation independent information further comprises a local estimate of the conduction velocity vector.

10. The system according to claim 9, wherein the local estimate of the conduction velocity vector occurs on a beat-by-beat basis.

11. A system for determining electrophysiological data, comprising:
an electronic control unit configured to:
receive electrical signals from a set of electrodes;
receive position and orientation data for the set of electrodes from a mapping system;
compensate for position and orientation artifacts of the set of electrodes;
compose cliques of a subset of neighboring electrodes in the set of electrodes, wherein each of the cliques comprise at least three electrodes, wherein the electrical signals comprise a plurality of bipole signals taken between the at least three neighboring electrodes in each of the cliques;
derive an E-field for a tissue adjacent to each of the cliques from the plurality of bipole signals, wherein bipole signals taken between the at least three neighboring electrodes in each of the cliques overdetermine the E-field for the tissue adjacent that clique;
determine catheter orientation independent information of a target tissue based on the electrogram data and position and orientation information from the set of electrodes, wherein the catheter orientation independent information comprises a local tangent E-field and an orthogonal unit vector in the direction along which a wavefront is propagating (a); and
output the orientation independent information to a display.

12. The system according to claim 11, wherein the orientation independent information further comprises a local estimate of the conduction velocity vector.

13. The system according to claim 11, wherein the electronic control unit is further configured to resolve the electrogram data into a 2D vector electrogram in a coordinate system of the mapping system.

14. The system according to claim 13, wherein the electrical signals comprises at least one planar electrode bipolar signal.

15. A method of determining electrophysiological data, comprising:
receiving electrogram data for a set of electrodes,
composing a clique of at least three neighboring electrodes from the set of electrodes, wherein the electrogram data comprises a plurality of bipole signals taken between the at least three neighboring electrodes in the clique;
receiving position and orientation information for the set of electrodes from a mapping system;
deriving an E-field from the plurality of bipole signals, wherein bipole signals taken between the at least three neighboring electrodes in the clique overdetermine the E-field;
determining catheter orientation independent information of a tissue based on the electrogram data and position and orientation information from the set of electrodes, wherein the catheter orientation independent information comprises a local tangent E-field and an orthogonal unit vector in the direction along which a wavefront is propagating (a); and
outputting the orientation independent information to a user or process.

16. The method according to claim 15, wherein the orientation independent information further comprises at least one of a 2D vector electric field, a 3D vector electric field, a normal electric field, the eccentricity of the tangent electric field loop, derived normal and tangent bipolar electrogram signals, a wavefront conduction velocity, or a unit direction vector.

17. The method according to claim 15 further comprising compensating for artifacts in the position and orientation information received from the mapping system.

18. The method according to claim 15 further comprising resolving the electrogram data into a 3D vector electrogram in a coordinate system of the mapping system.

19. The method according to claim 15, wherein the orientation independent information further comprises a local estimate of the conduction velocity vector.

20. The method according to claim 19, wherein the local estimate of the conduction velocity vector occurs on a beat-by-beat basis.

* * * * *